US006903183B1

(12) United States Patent
Stocco et al.

(10) Patent No.: US 6,903,183 B1

(45) Date of Patent: Jun. 7, 2005

(54) COMPOSITIONS AND METHODS FOR REGULATION OF STEROIDOGENESIS

(75) Inventors: Douglas M. Stocco, Lubbock, TX (US); Barbara J. Clark, Louisville, KY (US)

(73) Assignee: Texas Tech University Health Services Center, Lubbock, TX (US)

( * ) Notice: Subject to any disclaimer, the term of this patent is extended or adjusted under 35 U.S.C. 154(b) by 862 days.

(21) Appl. No.: 09/612,894

(22) Filed: Jul. 10, 2000

Related U.S. Application Data

(63) Continuation of application No. 08/659,254, filed on Jun. 7, 1996.

(51) Int. Cl.[7] .............................................. A61K 38/00

(52) U.S. Cl. ...................... 530/300; 530/350; 536/22.1; 435/6

(58) Field of Search ................................ 530/300, 350; 536/22.1; 435/6

(56) References Cited

U.S. PATENT DOCUMENTS 5,807,678 A * 9/1998 Miller et al. ................... 435/6

OTHER PUBLICATIONS

Clark, Barbara J. and Stocco, Douglas M., "Expression of a Novel LH–Induced Protein Responsible for the Acute Regulation of Steroidogenesis in Mouse Leydig Tumor Cells", Dallas IX International Congress on Hormonal Steroids, Sep. 24–29, 1994, Hyatt Regency at Reunion, Dallas, Texas, C185.

Clark, et al., "Expression of the Steroidogenic Acute Regulatory (StAR) Protein: A Novel LH–Induced Mitochondrial Protein Required for the Acute Regulation of Steroidogenesis in Mouse Leydig Tumor Cells", *Endocrine Research,* 21(1&2), 243–257 (1995).

Clark, et al., "Hormonal and Developmental Regulation of the Steroidogenic Acute Regulatory Protein", *Molecular Endocrinology,* vol. 9, No. 10, 1346–1355 (1995).

Clark, et al., "The Purification, Cloning, and Expression of a Novel Luteinizing Hormone–induced Mitochondrial Protein in MA–10 Mouse Leydig Tumor Cells", *The Journal of Biological Chemistry,* vol. 269, No. 45, Nov. 11, 1994, pp. 28314–28322.

Conference on the Adrenal Cortex, 1994.

Guo, et al., "Diagnosis of X–Linked Adrenal Hypoplasia Congenita by Mutation Analysis of the DAX1 Gene," *JAMA,* 274(4):324–330, Jul. 1995.

Hartung, et al., "Molecular Cloning and In Vivo Expression of the Bovine Steroidogenic Acute Regulatory Protein," *Biochemical and Biophysical Research Communications,* 215(2) :646–653, Oct. 1995.

(Continued)

*Primary Examiner*—Jezia Riley

(74) *Attorney, Agent, or Firm*—Cox & Smith Incorporated

(57) ABSTRACT

Compositions and methods relating to the regulation of transport of cholesterol into the mitochondria of a cell and, therefore, for the regulation of steroidogenesis are provided. Compositions include nucleic acid molecules encoding a steroidogenic acute regulatory protein (StAR), StAR protein molecules and peptides having amino acid sequences as disclosed herein, and anti-StAR antibodies. Methods include immunoassays using anti-StAR antibodies and nucleic acid based screening methods for pathologies correlated with defects in StAR, such as lipoid congenital adrenal hyperplasia and dose sensitive sex reversal. In addition, these compositions and methods may be useful for treatment of steroid hormone-dependent disorders, in particular, for lipoid congenital adrenal hyperplasia.

2 Claims, 7 Drawing Sheets

ATG
Sma1
Nde1
Sal 1
25
Pst1
Xho1
23rc
TAA
Not1
100bp

OTHER PUBLICATIONS

Huang, et al., "Corticotropin–Releasing Hormone (CRH) Stimulates Steroidogenesis in Mouse Leydig Cells", Society for the Study of Reproduction, Biology of Reproduction/vol. 50/Supplement 1, Jul. 24–27, 1994, 27th Annual Meeting, University of Michigan, Ann Arbor, Michigan.

Keyes, et al., "Steroidogenic Acute Regulatory Protein (StAR) in the Rabbit Corpus Luteum: Dependence Upon the Luteotrophic Hormone, 17B–Estradiol", Society for the Study of Reproduction, Biology of Reproduction/vol. 52/Supplement 1, 39, Jul. 9–12, 1995, 28th Annual Meeting, University of Michigan, Ann Arbor, Michigan.

King, et al., "Steroid Production after in Vitro Transcription, Translation, and Mitochondrial Processing of Protein Products of Complementary Deoxyribonucleic Acid for Steroidogenic Acute Regulatory Protein", *Endocrinology,* vol. 136, No. 11, 5165–5176 (1995).

Lin, D., et al., "Mutations in Steroidogenic Acute Regulatory Protein (StAR) Cause Congenital Lipoid Adrenal Hyperplasia (Lipoid CAH): Genetic Evidence for an Indispensible Role for StAR in Adrenal and Gonadal Steroidogenesis", Program & Abstracts, P3–620, 77th Annual Meeting, Jun. 14–17, 1995, Washington, D.C.

Lin, et al., "Role of Steroidogenic Acute Regulatory Protein in Adrenal and Gonadal Steroidogenesis", *Science,* vol. 267, pp. 1828–1831, Mar. 24, 1995.

Lipid Metabolism 1995, Kimball Union Academy, Meriden, NH, Jun. 25–30.

Muscatelll, et al., "Mutations in the DAX–1 Gene Give Rise To Both X–Linked Adrenal Hypoplasia Congenita and Hypogonadotropic Hypogonadism," *Nature,* 372:672–676, Dec. 1994.

Ronen–Fuhrmann, et al., "Steroidogenic Acute Regulatory Protein (StAR) : Immunocytochemical Characterization of a Novel Hormone–Induced Protein Required for the Acute Regulation of Steroidogenesis", Israel Endocrine Society, 1995.

Stocco, et al., "Role of the Steroidogenic Acute Regulatory Proten (StAR) in Steroidogenesis," *Biochemical Pharmacology,* 51:197–205, 1996.

Stocco, et al., "Regulation of the Acute Production of Steroids in Steroidogenic Cells," *Endocrine Reviews,*17(3) :1–24, Jun. 1996.

Stocco, et al., "Characterization of the Protein Responsible for the Acute Regulation of Steroidogenesis in Mouse Leydig Tumor Cells", XIII$^{th}$ Testis Workshop: Cellular and Molecular Regulation of Testicular Cells, Final Program and Abstract Book, Mar. 30–Apr. 1, 1995, Raleigh North Carolina, Serono Symposia USA.

Sugawara, et al., "Human steroidogenic acute regulatory protein: Functional activity in COS–1 cells, tissue–specific expression, and mapping of the structural gene to 8p11.2 and a pseudogen to chromosome 13", *Proc. Natl. Acad. Sci., U.S.A.,* vol. 92, pp. 4778–4782, May 1995.

Sugawara, et al., "Structure of the Human steroidogenic Acute Regulatory Protein (StAR) Gene: StAR Stimulates Mitochondrial Cholesterol 27–Hydroxylase Activity", *Biochemistry* (1995), 34:12506–12512.

Swain, et al., "Mouse DAX1 Expression is Consistent With a Role in Sex Determination as Well as in Adrenal and Hypothalamus Function," *Nature Genetics,* 12:404–409, Apr. 1996.

Yanase, et al., "New Mutations of DAX–1 Genes in Two Japanese Patients with X–Linked Congenital Adrenal Hypoplasia and Hypogonadotropic Hypogonadism," *Journal of Clinical Endrocrinology and Metabolism,* 81(2) :530–535, 1996.

Zanaria, et al., "An Unusual Member of the Nuclear Hormone Receptor Superfamily Responsible for X–Linked Adrenal Hypoplasia Congenita," *Nature,* 372:635–641, Dec. 1994.

Arensburg, et al., "Decidual and Giant Trophoblast Cell Expression of Steroidogenic Enzymes During Early Pregnancy in Mice," Second International Meeting on Molecular Steroidogenesis, 1996.

Balasubramanian, et al., "Regulation of Porcine Granulosa Cell Steroidogenic Acute Regulatory Protein (StAR) by Insulin–Like Growth Factor I: Synergism with Follicle––Stimulating Hormone or Protein Kinase A Agonist," *Endocrinology,* 138(1) :433–439, 1997.

Bose, et al., "The Pathophysiology and Genetics of Congenital Lipoid Adrenal Hyperplasia," *New England Journal of Medicine,* 335:1870–1878, Dec. 1996.

Choi, et al., "Diethylumbelliferyl Phosphate Inhibits Steroidogenesis by Interfering with a Long–Lived Factor Acting Between Protein Kinase A Activation and Induction of the Steroidogenic Acute Regulatory Protein (StAR)," *Eur. J. Biochem.,* 234:680–685, 1995.

Clark, B.J. & Stocco, D.M., "StAR–A Tissue Specific Acute Mediator of Steroidogenesis," *TEM,* 7(7) :227–233, 1996.

Pescador, et al., "Steroidogenic Acute Regulatory Protein in Bovine Corpora Lutea," *Biology of Reproduction,* 55:485–491, 1996.

Price, et al., "Evidence for Oestradiol Regulation of Steroidogenic Acute Regulatory Protein mRNA in Ram Testis," Society for the Study of Fertility, Nottingham, U.K., Jul. 15–17, 1996, to be published in the *Journal of Reproduction & Fertility Abstract Series,* 1996.

Rodgers, et al., "Concentrations of Steroid Acute Regulatory Protein, P450 Cholesterol Side–Chain Cleavage Enzyme and 3β–Hydroxysteroid Dehydrogenase During Prostaglandin F2α–Induced Luteal Regression in Cattle," Australian Society of Reproduction, Melbourne, Australia.

Stocco, et al., "Differential Effects of Dimethylsulfoxide on Steroidogenesis in Mouse MA–10 and Rat R2C Leydig Tumor Cells," *Endocrinology,* 136(7) :2993–2999, 1995.

Stocco, D.M. & Clark, B.J., "Corticotropin–Dependent Synthesis of Mitochondrial Proteins Involved in the Acute Regulation of Steroidogenesis," *Endocrinology and Diabetes,* 3:195–201, 1996.

Townson, et al., "Expression of the Steroidogenic Acute Regulatory Protein in the Corpus Luteum o the Rabbit: Dependence Upon the Luteotropic Hormone, Estradiol–17β[1]," *Biology of Reproduction,* 55:868–874, 1996.

Stocco, et al., "Immunocytochemical Localization of the Steroidogenic Acute Regulatory Protein (StAR) in Steroidogenic Tissues," Annual Meeting of the Society for the Study of Reproduction, Davis, California, 1995.

King, et al., "Steroidogenic Acute Regulatory (StAR) Protein Induces Steroid Production in Isolated Mitochondria," Annual Meeting of the Society for the Study of Reproduction, Davis, California, 1995.

Orley, et al., "Expression of Steroidogenic Acute Regulatory Protein (StAR) During Follicular Development in Rat Ovary," Annual Meeting of the Society for the Study of Reproduction, Davis, California, 1995.

Liu, et al., "Expression of the Steroidogenic Acute Regulatory Protein mRNA in Human Adrenal Tumors and Cultured Adrenal Cells," 10th International Congress of Endocrinology, 1996.
Cherradi, et al. "Calcium Stimulates Intramitochondrial Cholesterol Transfer and StAR Protein in Bovine Adrenal Glomerulosa Cells," 10th International Congress of Endocrinology, 1996.
Hales, et al., "Inhibition of Serum Testosterone by Endotoxin Parallels Loss of Steroidogenic Acute Regulatory (StAR) Protein in Mouse Leydig Cells," 10th International Congress of Endocrinology, 1996.
McLean, et al., "Rapid and Coordinated Reduction in Ovarian Sterol Carrier Protein–2 and Steroidogenesis Acute Regulatory Protein mRNA Levels Following PGF2α Administration," 10th International Congress of Endocrinology, 1996.
Portrat–Doven, et al., "Three New Mutations of the Steroidogenic Acute Regulatory Gene (StAR) in 2 Families with Congenital Lipoid Adrenal Hyperplasia," 10th International Congress of Endocrinology, 1996.
Fujieda, et al., "Molecular Analysis of the Steroidogenic Acute Regulatory Protein (StAR) Gene from 23 Japanese Patients with Congenital Lipoid Adrenal Hyperplasia," 10th International Congress of Endocrinology, 1996.
Sridaran, et al., "LHRH Antagonist (NAL–LYS Antagonist: Antide) Suppresses the Luteal Steroidogenesis During Pregnancy in the Rat," 10th International Congress of Endocrinology, 1996.
Pezzi, et al., "Role of Calmodulin–Dependent Protein Kinase in an Acute Adrenal Aldosterone Production," 10th International Congress of Endocrinology, 1996.
Chedrese, et al., "FSH, LH and Estradol–17β ($E_2$) Stimulates Steroidogenic Acute Regulatory (StAR) Protein–Gene Expression in Cultured Porcine Granulosa Cells," Society for the Study of Reproduction 29th Annual Meeting, London, Ontario Canada, Jul. 1996.

Wang, et al., "Specific Binding of the Steroidogenic Acute Regulatory (StAR) Protein to a Mitochondrial Membrane Protein Complex," Society for the Study of Reproduction 29th Annual Meeting, London, Ontario Canada, Jul. 1996.

Sridaran, et al., "Steroidogenic Acute Regulatory Protein (StAR) in the Rat Corpus Luteum: Its Inhibition by a GnRH Agonist," Society for the Study of Reproduction 29th Annual Meeting, London, Ontario Canada, Jul. 1996.

Huang, et al., Corticotropin–Releasing Hormone (CRH) Stimulates the Expression of 30–kDa StAR (Steroidogenesis Acute Regulatory) Mitochondrial Protein in MA–10 Cells., Society for the Study of Reproduction 29th Annual Meeting, London, Ontario Canada, Jul. 1996.

King, et al., "Importance of the Phosphorylation State of the Steroidogenic Acute Regulatory (StAR) Protein for Steroidogenesis," Society for the Study of Reproduction 29th Annual Meeting, London, Ontario Canada, Jul. 1996.

Liu, et al., "Does Cholesterol Bind to the Steroidogenic Acute Regulatory (StAR) Protein?" Society for the Study of Reproduction 29th Annual Meeting, London, Ontario Canada, Jul. 1996.

* cited by examiner

FIG. 2A 1 gtcgacccacgcgtccgctcaggaccttgaaaggctcaggaagaacaaccctTGAgcacc
61 tcagcactcagcATGTTCCTCGCTACGTTCAAGCTGTGTGCTGGAAGCTCCTATAGACAT
MetPheLeuAlaThrPheLysLeuCysAlaGlySerSerTyrArgHis 16

121 ATGCGGAATATGAAAGGATTAAGGCACCAAGCTGTGCTGGCCATTGGCCAAGAGCTCAAC
MetArgAsnMetLysGlyLeuArgHisGlnAlaValLeuAlaIleGlyGlnGluLeuAsn 36

181 TGGAGAGCACTGGGGGATTCCAGTCCCGGGTGGATGGGTCAAGTTCGACGTCGGAGCTCT
TrpArgAlaLeuGlyAspSerSerProGlyTrpMetGlyGlnValArgArgArgSerSer 56

241 CTGCTTGGTTCTCAACTGGAAGCAACACTCTATAGTGACCAGGAGCTGTCCTACATCCAG
LeuLeuGlySerGlnLeuGluAlaThrLeuTyrSerAspGlnGluLeuSerTyrIleGln 76

301 CAGGGAGAGGTGGCTATGCAGAAGGCCTTGGGCATACTCAACAACCAGGAAGGCTGGAAG
GlnGlyGluValAlaMetGlnLysAlaLeuGlyIleLeuAsnAsnGlnGluGlyTrpLys 96
25

361 AAGGAAAGCCAGCAGGAGAACGGGGACGAAGTGCTAAGTAAGATGGTGCCAGATGTGGGC
LysGluSerGlnGlnGluAsnGlyAspGluValLeuSerLysMetValProAspValGly 116

421 AAGGTGTTTCGCTTGGAGGTGGTGGTAGACCAGCCCATGGACAGACTCTATGAAGAACTT
LysValPheArgLeuGluValValValAspGlnProMetAspArgLeuTyrGluGluLeu 136

481 GTGGACCGCATGGAGGCCATGGGAGAGTGGAACCCAAATGTCAAGGAGATCAAGGTCCTG
ValAspArgMetGluAlaMetGlyGluTrpAsnProAsnValLysGluIleLysValLeu 156

541 CAGAGGATTGGAAAAGACACGGTCATCACTCATGAGCTGGCTGCGGCGGCAGCAGGCAAC
GlnArgIleGlyLysAspThrValIleThrHisGluLeuAlaAlaAlaAlaAlaGlyAsn 176

601 CTGGTGGGGCCTCGAGACTTCGTGAGCGTGCGCTGTACCAAGCGCAGAGGTTCCACCTGT
LeuValGlyProArgAspPheValSerValArgCysThrLysArgArgGlySerThrCys 196

661 GTGCTGGCAGGCATGGCCACACATTTTGGGGAGATGCCGGAGCAGAGTGGTGTCATCAGA
ValLeuAlaGlyMetAlaThrHisPheGlyGluMetProGluGlnSerGlyValIleArg 216
45

721 GCTGAACACGGCCCCACCTGCATGGTGCTTCATCCACTGGCTGGAAGTCCCTCCAAGACT
AlaGluHisGlyProThrCysMetValLeuHisProLeuAlaGlySerProSerLysThr 236
23

781 AAACTCACTTGGCTGCTCAGTATTGACCTGAAGGGGTGGCTGCCGAAGACAATCATCAAC
LysLeuThrTrpLeuLeuSerIleAspLeuLysGlyTrpLeuProLysThrIleIleAsn 256

FIG. 2B

```
841 CAGGTCCTATCGCAGACCCAGATAGAGTTCGCCAACCACCTGCGCAAGCGCCTGGAAGCC
    GlnValLeuSerGlnThrGlnIleGluPheAlaAsnHisLeuArgLysArgLeuGluAla 276

901 AGCCCTGCCTCTGAGGCCCAGTGTTAAggactgtccaccacattgacctgcaaatcattg
    SerProAlaSerGluAlaGlnCysEnd                                  284

 961 gaagctctcacaggaagcctgcaagtctgtccatcttcagctaacagcatcgggaggggt
1021 ggtagtcaggagacactaggactgactggtaaaatcaggatcagcaaaatagaaatgagg
1081 cttagaataaaagttctctagtgtctcccactgcatagctgtgaaggctaagggataagt
1141 agctatgaaacctttcatctaggcttgtatatgctgacctaaaagacaccagcagctacg
1201 aacaggggatgctaaggatcgggaactgttgtcttaccagctccaaatgtcactacctga
1261 aggcagtgtgcacacaaagcaaggtcttgcctaggaaactctgtaaaagttctcctctgt
1321 aaaaggccagaacttgaatgaaactacctacaaagggcctttccagagtattccaacttt
1381 tctctgaggagaaatgaaaccatcattgtgccgacttccctactaatcccatgacAATAA
1441 AgaacatacatAAAAAAAAAAAAAA
```

FIG. 3A

Human steroidogenic acute regulatory protein (StAR) mRNA.

Length = 1605

Identities = 104/134 (77% identity). mouse segment 73-206 to human segment 127-260:

```
Mouse:   73 ATGTTCCTCGCTACGTTCAAGCTGTGTGCTGGAAGCTCCTATAGACATATGCGGAATATG 132
            ||| | || || || ||||||||||| ||||| |||||||| ||||| ||||| || |||
Human:  127 ATGCTGCTAGCGACATTCAAGCTGTGCGCTGGGAGCTCCTACAGACACATGCGCAACATG 186

Mouse:  133 AAAGGATTAAGGCACCAAGCTGTGCTGGCCATTGGCCAAGAGCTCAACTGGAGAGCACTG 192
            || ||  | ||||| || |||||| |||||||  |||| |||| ||| |||| || |||
Human:  187 AAGGGGCTGAGGCAACAGGCTGTGATGGCCATCAGCCAGGAGCTGAACCGGAGGGCCCTG 246

Mouse:  193 GGGGATTCCAGTCC  206
            ||||   |||  ||
Human:  247 GGGGGCCCCACCCC  260
```

Identities = 612/722 (84% identity); mouse segment 210-931 to human segment 267-988:

```
Mouse:  210 GTGGATGGGTCAAGTTCGACGTCGGAGCTCTCTGCTTGGTTCTCAACTGGAAGCAACACT 269
            ||||||    || ||||| || ||||||||||| || |||||||  |||||||  || ||
Human:  267 GTGGATTAACCAGGTTCGGCGGCGGAGCTCTCTACTCGGTTCTCGGCTGGAAGAGACTCT 326

Mouse:  270 CTATAGTGACCAGGAGCTGTCCTACATCCAGCAGGGAGAGGTGGCTATGCAGAAGGCCTT 329
            ||| ||||||||||||||| ||||  |||||||||| |||| ||| ||||||||||||||
Human:  327 CTACAGTGACCAGGAGCTGGCCTATCTCCAGCAGGGGGAGGAGGCCATGCAGAAGGCCTT 386

Mouse:  330 GGGCATACTCAACAACCAGGAAGGCTGGAAGAAGGAAAGCCAGCAGGAGAACGGGGACGA 389
            |||||| || | |||||| || |||||||||||||| || |||||||| || |||||| |
Human:  387 GGGCATCCTTAGCAACCAAGAGGGCTGGAAGAAGGAGAGTCAGCAGGACAATGGGGACAA 446

Mouse:  390 AGTGCTAAGTAAGATGGTGCCAGATGTGGGCAAGGTGTTTCGCTTGGAGGTGGTGGTAGA 449
            |||| | |||||  |||| |||||||||||||||||||| ||  ||||||| ||||| ||
Human:  447 AGTGATGAGTAAAGTGGTCCCAGATGTGGGCAAGGTGTTCCGGCTGGAGGTCGTGGTGGA 506
```

FIG. 3B

```
Mouse:  450 CCAGCCCATGGACAGACTCTATGAAGAACTTGTGGACCGCATGGAGGCCATGGGAGAGTG 509
            ||||||||||||| || ||||||||| || ||||| |||||||| || ||||| |||||
Human:  507 CCAGCCCATGGAGAGGCTCTATGAAGAGCTCGTGGAGCGCATGGAAGCAATGGGGGAGTG 566

Mouse:  510 GAACCCAAATGTCAAGGAGATCAAGGTCCTGCAGAGGATTGGAAAAGACACGGTCATCAC 569
            |||||| ||||||||||||||||||||||||||||| ||| |||||||| ||  |||| ||
Human:  567 GAACCCCAATGTCAAGGAGATCAAGGTCCTGCAGAAGATCGGAAAAGATACATTCATTAC 626

Mouse:  570 TCATGAGCTGGCTGCGGCGGCAGCAGGCAACCTGGTGGGGCCTCGAGACTTCGTGAGCGT 629
            ||| ||||||||||| | ||||||||| |||||||||||||| || ||||| ||||||||
Human:  627 TCACGAGCTGGCTGCCGAGGCAGCAGGAAACCTGGTGGGGCCCCGTGACTTTGTGAGCGT 686

Mouse:  630 GCGCTGTACCAAGCGCAGAGGTTCCACCTGTGTGCTGGCAGGCATGGCCACACATTTTGG 689
            ||||||| |||||||| |||| ||||||||||||||||| ||||||| |||| | || ||
Human:  687 GCGCTGTGCCAAGCGCCGAGGCTCCACCTGTGTGCTGGCTGGCATGGACACAGACTTCGG 746

Mouse:  690 GGAGATGCCGGAGCAGAGTGGTGTCATCAGAGCTGAACACGGCCCCACCTGCATGGTGCT 749
            | | ||||| |||||||  |||||||||||| || || ||||| ||||| ||||||||||
Human:  747 GAACATGCCTGAGCAGAAGGGTGTCATCAGGGCGGAGCACGGTCCCACTTGCATGGTGCT 806

Mouse:  750 TCATCCACTGGCTGGAAGTCCCTCCAAGACTAAACTCACTTGGCTGCTCAGTATTGACCT 809
            ||| ||  |||||||||||||||| ||||| ||||| || ||||| ||||| || |||||
Human:  807 TCACCCGTTGGCTGGAAGTCCCTCTAAGACCAAACTTACGTGGCTACTCAGCATCGACCT 866

Mouse:  810 GAAGGGGTGGCTGCCGAAGACAATCATCAACCAGGTCCTATCGCAGACCCAGATAGAGTT 869
             |||||||||||||| ||||  ||||||||||||||||| || ||||||||| | || ||
Human:  867 CAAGGGGTGGCTGCCCAAGAGCATCATCAACCAGGTCCTGTCCCAGACCCAGGTGGATTT 926

Mouse:  870 CGCCAACCACCTGCGCAAGCGCCTGGAAGCCAGCCCTGCCTCTGAGGCCCAGTGTTAAGG 929
             ||||||||||||||||||||||||||  ||  ||||||||||||| |||  ||||| | |
Human:  927 TGCCAACCACCTGCGCAAGCGCCTGGAGTCCCACCCTGCCTCTGAAGCCAGGTGTTGAAG 986

Mouse:  930 AC          931
            ||
Human:  987 AC          988
```

Identities = 18/19 (94% identity), mouse segment 970-988 to human segment 1051-1069

```
Mouse:  970  ACAGGAAGCCTGCAAGTCT    988
             || ||||||||||||||||
Human: 1051  ACTGGAAGCCTGCAAGTCT    1069
```

FIG. 5

```
                                                        C1          C2
Bovine   1  MLLATFKLCA  GSSYRHvRsM  KGLqQQAVLA  IGQELNRRAL  GGPaPaaWIN  50
Human       MLLATFKLCA  GSSYRHMRNM  KGLRQQAVMA  IsQELNRRAL  GGPtPstWIN
Mouse       MFLATFKLCA  GSSYRHMRNM  KGLRhQAVLA  IGQELNWRAL  GdssPg.Wmg
Ovine       ..........  ..........  ..........  ..........  ..........
Consensus   MLLATFKLCA  GSSYRHMRNM  KGLRQQAVLA  IGQELNRRAL  GGP-P--WIN

                     A       CK
Bovine  51  QVRRRgSLLG  SQLEDpLYSD  QELAhIQQGE  EAMQrALGIL  kdQEGWKKES  100
Human       QVRRRSSLLG  SrLEETLYSD  QELAYIQQGE  EAMQKALGIL  sNQEGWKKES
Mouse       QVRRRSSLLG  SQLEaTLYSD  QELsYIQQGE  vAMQKALGIL  nNQEGWKKES
Ovine       ..........  ..........  ..........  ..........  ......KKEn
Consensus   QVRRRSSLLG  SQLE-TLYSD  QELAYIQQGE  EAMQKALGIL  -NQEGWKKES

Bovine 101  rQaNGDEVLS  KVIPDVGKVF  RLEVVVDQPM  ERLYEELVER  MEAMGEWNPN  150
Human       qQdNGDkVMS  KVVPDVGKVF  RLEVVVDQPM  ERLYEELVER  MEAMGEWNPN
Mouse       qQeNGDEVLS  KmVPDVGKVF  RLEVVVDQPM  DRLYEELVDR  MEAMGEWNPN
Ovine       rQaNGDEVLS  KVIPDVGKVF  RLEVVVDQPM  ERLYEELVER  MEAMGEWNPs
Consensus   -Q-NGDEVLS  KV-PDVGKVF  RLEVVVDQPM  ERLYEELVER  MEAMGEWNPN

                                                                 A
Bovine 151  VKEIKVLQKI  GKDTVITHEL  AAEvAGNLVG  PRDFVSVRCT  KRRGSmCVLA  200
Human       VKEIKVLQKI  GKDTfITHEL  AAEAAGNLVG  PRDFVSVRCa  KRRGStCVLA
Mouse       VKEIKVLQrI  GKDTVITHEL  AAaAAGNLVG  PRDFVSVRCT  KRRGStCVLA
Ovine       VKEIKVLQKI  GKDTIITHEL  AAEAAGNLVG  PRDFVrVRCT  KRRGSmCVLA
Consensus   VKEIKVLQKI  GKDTVITHEL  AAEAAGNLVG  PRDFVSVRCT  KRRGS-CVLA

                                                 CD   C
Bovine 201  GMATLYeEMP  qQKGVIRAEH  GPTCMVLrPL  AGSPSrTKLT  WLLSIDLKGW  250
Human       GMdTdFgnMP  eQKGVIRAEH  GPTCMVLHPL  AGSPSKTKLT  WLLSIDLKGW
Mouse       GMAThFgEMP  eQsGVIRAEH  GPTCMVLHPL  AGSPSKTKLT  WLLSIDLKGW
Ovine       GtATLYeEMP  qQKGVIR...  ..........  ..........  ..........
Consensus   GMATL--EMP  -QKGVIRAEH  GPTCMVLHPL  AGSPSKTKLT  WLLSIDLKGW

Bovine 251  LPKTIINQVL  SQTQVDFANH  LRKRLEScPA  lEARC 285
Human       LPKsIINQVL  SQTQVDFANH  LRKRLEShPA  SEARC
Mouse       LPKTIINQVL  SQTQIEFANH  LRKRLEasPA  SEAqC
Ovine       ..........  ..........  ..........  .....
Consensus   LPKTIINQVL  SQTQVDFANH  LRKRLES-PA  SEARC
```

COMPOSITIONS AND METHODS FOR REGULATION OF STEROIDOGENESIS

The present application is a continuation application of U.S. Ser. No. 08/659,254 filed Jun. 7, 1996, now allowed. That disclosure is incorporated herein by reference in its entirety.

The government owns certain rights in the present invention purusant to grant numbers HD17481 and HD07688 from the National Institutes of Health.

FIELD OF THE INVENTION

The present invention relates generally to compositions and methods for the regulation of steroidogenesis. More particularly, it concerns compositions and methods relating to the regulation of transport of cholesterol into the mitochondria of a cell for the synthesis of androgens, estrogens, glucocorticoids, mineralocorticoids, and progestagens. The invention also relates to methods for detecting and treating steroid hormone-dependent disorders. The nucleic acid molecules of the present invention also provide methods for screening a sample for steroid hormone-dependent disorders, as well as to methods for preparing recombinant proteins for StAR. The invention further relates to the field of nucleic acid probes and primers, as the various nucleic acid molecules of the invention may be used as molecular probes in all of the aforedescribed methods, as well as primers for amplifying particular sequences of interest.

BACKGROUND OF THE INVENTION

The testis is known to be the source of circulating androgens that are responsible for the maintenance of the secondary sexual characteristics in the male. In most species the testis has two separate compartments: the seminiferous tubules that contain the Sertoli cells, the peritubular cells, and the germ cells; and the interstitial compartment that contains the Leydig cells, macrophages, lymphocytes, granulocytes and the cells composing the blood, nerve and lymphatic structures.

The Leydig cells, located in the interstitial compartment and comprising approximately 2–3% of the total testicular cell number in most species, are the only cells in the testis that contain two key steroidogenic enzymes, namely, cytochrome P450 side chain cleavage (P450scc) and 3 beta-hydroxysteroid dehydrogenase (3 beta-HSD). Thus, Leydig cells are the only testicular cells capable of the first two steps in steroidogenesis; i) the conversion of cholesterol, the substrate for all steroid hormones, to pregnenolone; and ii) conversion of pregnenolone to progesterone. Therefore, the interstitial compartment in general, and the Leydig cells in particular synthesize virtually all of the steroids produced in the testis, with testosterone being the major steroid biosynthesized.

The major stimulus for the biosynthesis of testosterone in the Leydig cell is the gonadotrophic hormone, luteinizing hormone (LH). LH is secreted from specific cells located in the anterior pituitary and it interacts with specific receptors on the surface of the Leydig cell and initiates the signal for testosterone production. Cellular events occur rapidly in response to the trophic hormone stimulation of Leydig cells, and result in the synthesis and secretion of testosterone. These rapid or acute effects of hormone stimulation occur within minutes and can be distinguished temporally from the slower chronic effects that occur on the order of many hours and that involve mechanisms to increase gene transcription and translation of the steroid hydroxylase cytochrome P450 enzymes involved in the biosynthesis of these steroids.

The rate-limiting enzymatic step in steroidogenesis is the conversion of cholesterol to pregnenolone by the cholesterol side-chain cleavage complex (CSCC) which is localized to the mitochondrial inner membrane (Stone and Hechter, 1954; Karaboyas and Koritz, 1965; Simpson, et al. 1972). However, the delivery of the substrate cholesterol from cellular stores and the outer mitochondrial membrane to the inner mitochondrial membrane and the CSCC is the true regulated, rate-limiting step in this process (Crivello and Jefcoate, 1980; Jefcoate, et al., 1987). Cycloheximide, an inhibitor of protein synthesis, blocks the hormone-induced steroid production in two steroidogenic tissues of the rat; the adrenal and testis (Ferguson, 1963; Garren, et al., 1965; Davis and Garren, 1968; Jefcoate et al., 1974; Mendelson et al., 1975; Cooke, et al., 1975). This block is at the point of transfer of cholesterol from the outer to the inner mitochondrial membrane and the CSCC (Simpson et al., 1972; Privalle et al. 1983). Therefore, acute regulation of steroidogenesis requires de novo protein synthesis (Jefcoate et al., 1986).

During protein import into the mitochondrial matrix, the inner and outer mitochondrial membranes become closely associated and form protein translocation "contact sites" (Schleyer and Neupert, 1985; Schwaiger et al., 1987; Glick, et al., 1991). Phospholipids are transferred from the outer mitochondrial membrane to the inner mitochondrial membrane at these membrane "contact sites" (Simbeni et al., 1990; Simbeni et al., 1991; Ardail et al., 1991). Therefore, the intramitochondrial cholesterol translocation required for steroidogenesis may also occur at membrane contact sites. An increase in intrrmitochondrial membrane contacts by a hormone-dependent, cycloheximide-sensitive mechanism may regulate cholesterol transport to the CSCC (Jefcoate, et al., 1986). Thus, in the acute regulation of steroidogenesis, a putative function for the newly synthesized regulatory protein may be to facilitate the formation of mitochondrial contact sites that would result in an increased rate of transfer of cholesterol to the inner membrane and CSCC which ultimately would result in the observed increase in the rate of steroid production. However, the search for these cycloheximide-sensitive regulatory protein(s) has been ongoing for nearly 30 years, but, as yet, the mechanism of cholesterol transfer to the CSCC is not known.

The present inventors have previously identified a family of hormone-induced mitochondrial proteins in MA-10 cells that regulate cholesterol delivery to the inner mitochondrial membrane and the CSCC. These proteins have been described as the mitochondrial 37 kDa, 32 kDa, and 30 kDa molecular weight proteins and they are synthesized in response to either LH and hCG or by stimulation with the CAMP analogue, $Bt_2cAMP$ (Stocco and Kilgore, 1988). The 30 kDa species consists of four separate proteins and proteolytic digestion of all four forms indicates that they are all modified forms of the same protein (Stocco and Chen, 1991). Pulse chase experiments and tryptic peptide mapping of the 37 kDa and 30 kDa proteins indicated that the 37 kDa form is a precursor to the 30 kDa protein (Stocco and Sodeman, 1991; Epstein and Orne-Johnson, 1991). These reports, however, lack information regarding the structure of the nucleic acid molecules and protein molecules involved in steroidogenesis.

Lipoid congenital adrenal hyperplasia (LCAH) is a lethal autosomal recessive disease that results in a complete inability of a newborn infant to synthesize steroids. The lack of mineralocorticoids and glucocorticoids results in death within days to weeks of birth if not detected and treated with adequate steroid hormone replacement therapy. This condition is manifested by the presence of large adrenals containing very high levels of cholesterol and cholesterol esters and also by an increased amount of lipid accumulation in testicular Leydig cells, though this level is somewhat lower than that seen in adrenals. As isolated, mitochondria from adrenals and gonads of affected patients cannot convert cholesterol to pregnenolone (Camacho et al., 1968; Degenhart et al., 1972; Koizumi et al., Hauffa et al., 1985). The P450scc enzyme that converts cholesterol to pregnenolone has been shown to be normal in patients who suffered from this disease (Lin et al., 1991). Thus, the defect lies upstream of P450scc at the point of cholesterol delivery to the enzyme.

Prior art lacks sufficient identification of the agent(s) responsible for the LCAH metabolic defect and defects in cholesterol transport, lacks screening methods for their detection, and lacks provision of pharmacological agents effective in alleviating the defects. Because of these problems, known procedures are not completely satisfactory despite efforts of persons skilled in the art, and the present inventors have searched for improvements. Further characterization of agents involved in these defects at the amino acid and nucleic acid levels would provide potential solutions and alternatives to resolving these and other problems in the art.

SUMMARY OF THE INVENTION

The present invention seeks to overcome these and other drawbacks inherent in the prior art by providing compositions and methods including the nucleotide sequence of the gene encoding a steroidogenic acute regulatory protein (StAR) protein, or compositions that include a protein having the amino acid sequence of the StAR protein. The fundamental importance of the StAR protein is that it is the acute regulator of a key step in the steroidogenic biosynthetic pathway. Importantly, the production of mineralocorticoids, glucocorticoids, and sex hormones are dependent on the expression of this protein.

Nucleic acid molecules having nucleotide sequences of the gene encoding StAR may be used in a variety of different diagnostic applications, including the evaluation of gene defects associated with steroid hormone production. The hormonally induced, CAMP-mediated acute regulation of steroid hormone biosynthesis in steroidogenic cells is characterized by the mobilization of cholesterol from cellular stores to the mitochondria outer membrane, and its translocation to the inner membrane where the conversion of cholesterol to pregnenolone occurs. Steroid hormone-dependent disorders that may be addressed using compositions and methods of the present invention include lipoid congenital adrenal hyperplasia, infertility, sexual maturation, androgen-responsive tumors, precocious puberty, McCune-Albright syndrome, adrenal-hypoplasia congenita, or hypogonadotropic hypogonadism.

Further, in pregnancy induced diabetes, progesterone levels are lower than normal and the fetus may be aborted spontaneously. The level of StAR protein may be deficient in these patients and it may be possible as a result of the present invention to monitor levels of StAR in pregnancy for predicting patients that may be at risk for spontaneous abortion.

The nucleic acid molecules of the invention may further be used to provide recombinant preparations of the StAR protein. These highly purified preparations can also be provided in relatively high yield in conjunction with techniques well known to those of skill in the art of recombinant technology.

In certain aspects, the invention relates to a purified nucleic acid molecule having a nucleotide sequence encoding a steroidogenic acute regulatory protein, the protein having an amino acid sequence as set forth in SEQ ID NO: 2 or SEQ ID NO:18, or sequences that are about 80% to about 99% identical to that sequence. "Purified" nucleic acid molecules having a nucleotide sequence encoding steroidogenic acute regulatory protein (StAR), in some embodiments of the invention, means a StAR encoding nucleic acid molecule substantially free of nucleic acid molecules not encoding an amino acid sequence having about 80% to about 99% identity to the sequence set forth in SEQ ID NO:2 or SEQ ID NO:18. A further embodiment of the invention is a purified nucleic acid molecule having a nucleotide sequence encoding a steroidogenic acute regulatory protein antigen, the antigen having an amino acid sequence having about 80% to about 99% identity to the sequence set forth in SEQ ID NO:8, and the nucleic acid molecule being substantially free of nucleic acid molecules not encoding the steroidogenic acute regulatory protein antigen.

The term "essentially as set forth in SEQ ID NO:2, SEQ ID NO:18 or SEQ ID NO:8" means that the sequence substantially corresponds to a portion of the indicated sequence and has relatively few amino acids which are not identical to, or a biologically functional equivalent of, the amino acids set forth. The term "biologically functional equivalent" is well understood in the art and is further defined as a protein having a sequence essentially as set forth in the indicated SEQ ID NO, and that is involved in the transfer of cholesterol from cellular stores to the inner mitochondrial membrane. Accordingly, sequences which have between about 70% and about 80%; or more preferably, between about 81% and about 90%; or even more preferably, between about 91% and about 99%; of amino acids that are identical or functionally equivalent to the amino acids of the indicated SEQ ID NO:2, 18, or 8 will be sequences which are "essentially as set forth in SEQ ID NO:2, 18, or 8".

Some embodiments of the above-described nucleic acid molecule are those wherein the steroidogenic acute regulatory protein has the amino acid sequence of SEQ ID NO: 2 or 18. In further defined embodiments, the invention provides the above-described nucleic acid molecule wherein the amino acid sequence begins with amino acid methionine at position 48 of SEQ ID NO:2 and extends through amino acid cysteine at position 284 of SEQ ID NO:2. Amino acids 1–47 constitute the signal sequence which is cleaved during processing to the mature protein as described in Example 2.

A further embodiment of the present invention is where the nucleic acid molecule has a nucleotide sequence as set forth in SEQ ID NO: 1 or 19, and preferably, the nucleic acid molecule is further defined as including a detectable label.

Nucleic Acids

Some embodiments of the present invention provide purified nucleic acid molecules that encode StAR protein having an amino acid sequence essentially as set forth in SEQ ID NO:2 or 18. As used herein, the terms "nucleic acid molecule" may refer to a DNA or RNA molecule which has been isolated free of total genomic DNA, or free of total RNA, of a particular species. Therefore, a "purified" nucleic acid molecule as used herein, refers to a nucleic acid molecule that contains a StAR coding sequence yet is isolated away from, or purified free from, total genomic DNA or total RNA, for example, total human genomic DNA. Included within the term "DNA molecule", are DNA segments and smaller fragments of such segments, and also recombinant vectors, including, for example, plasmids, cosmids, phage, viruses, and the like.

Another embodiment of the present invention is a purified nucleic acid molecule, further defined as including a nucleotide sequence in accordance with SEQ ID NO:1 or 19. In some embodiments, the purified nucleic acid segment comprises a nucleotide sequence having about 75% to about 99% identity with the sequence at SEQ ID NO:1 or with the StAR coding sequences thereof (see FIG. 3). Such nucleotide sequences are more particularly defined as being substantially free of nucleic acids not encoding the StAR protein.

Similarly, a DNA molecule comprising an isolated or purified StAR gene refers to a DNA molecule including StAR coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, cDNA sequences or combinations thereof. "Isolated substantially away from other coding sequences" means that the gene of interest, in this case the StAR encoding gene, forms the significant part of the coding region of the DNA molecule, and that the DNA molecule does not contain large portions of naturally-occurring coding DNA, such as large chromosomal fragments or other functional genes or cDNA coding regions. Of course, this refers to the DNA molecule as originally isolated, and does not exclude genes or coding regions later added to the segment by the hand of man.

Another embodiment of the present invention is a purified nucleic acid molecule that encodes a protein having a sequence with about 80% to about 99% identity to SEQ ID NO:2 or 18, further defined as a recombinant vector. As used herein, the term "recombinant vector", refers to a vector that has been modified to contain a nucleic acid segment that encodes a StAR protein, or fragment of interest thereof The recombinant vector may be further defined as an expression vector comprising a promoter operatively linked to said StAR encoding nucleic acid molecule. In some embodiments, the recombinant vector comprises a nucleic acid sequence in accordance with SEQ ID NO:1 or 19, or with about 80% to about 99% identity to the sequence of SEQ ID NO:1 or 19. By way of example and not limitation, vectors may be further defined as a pCMV, pUC and derivatives thereof, SV40, adenoviral, retroviral, yeast plasmids, *Baculovirus* or *Vaccinia* virus vector.

A further preferred embodiment of the present invention is a host cell, made recombinant with a recombinant vector comprising a StAR gene. The recombinant host cell may be a prokaryotic or a eukaryotic cell. In a more preferred embodiment, the recombinant host cell is a eukaryotic cell. As used herein, the term "engineered" or "recombinant" cell is intended to refer to a cell into which a recombinant gene, such as a gene encoding StAR, has been introduced. Therefore, engineered cells are distinguishable from naturally occurring cells which do not contain a recombinantly introduced gene. Thus, engineered cells are cells having a gene or genes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene, or combinations thereof. Preferred host cells may be further defined as a Leydig cell (primary or MA-10 cells), an adrenalcortical cell such as the H295 human adrenalcortical cell line, a primary culture ovarian granulosa cell, a COS cell, *Saccharomyces cerevisiae,* or *Escherichia coli* cell.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventors do not exclude the possibility of employing a genomic version of a particular gene where desired.

In certain embodiments, the invention concerns isolated DNA molecules and recombinant vectors which encode a protein or peptide that includes within its amino acid sequence an amino acid sequence essentially as set forth in SEQ ID NO:2 or 18. Naturally, where the DNA segment or vector encodes a fall length StAR protein, or is intended for use in expressing the StAR protein, the most preferred sequences are those which are essentially as set forth in SEQ ID NO:2 or 18.

In certain other embodiments, the invention concerns isolated DNA segments and recombinant vectors that include within their sequence a nucleic acid sequence essentially as set forth in SEQ ID NO:1 or 19. The term "essentially as set forth in SEQ ID NO:1 or 19", is used in the same sense as described above and means that the nucleic acid sequence substantially corresponds to a portion of SEQ ID NO:1 or 19, and has relatively few codons which are not identical, or functionally equivalent, to the codons of SEQ ID NO:1 or 19. The term "functionally equivalent codon" is used herein to refer to codons that encode the same amino acid, such as the six codons for arginine or serine, as set forth in Table 1, and also refers to codons that encode biologically equivalent amino acids.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes. The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably.

Excepting intronic or flanking regions, and allowing for the degeneracy of the genetic code, sequences which have between about 70% and about 90%; or more preferably, between about 80% and about 90%; or between about 80% and about 99%; of nucleotides which are identical to the nucleotides of SEQ ID NO:1 or 19 will be sequences which are "essentially as set forth in SEQ ID NO:1 or 19". Sequences which are essentially the same as those set forth in SEQ ID NO:1 or 19 may also be functionally defined as sequences which are capable of hybridizing to a nucleic acid segment containing the complement of SEQ ID NO:1 or 19 under relatively stringent conditions. Suitable relatively stringent hybridization conditions will be well known to those of skill in the art and are clearly set forth herein, for example conditions for use with Northern blot analysis, and as described in the various embodiments of the invention provided herein and particularly in Example 2.

TABLE 1

CODON DEGENERACY

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

The present invention includes a purified nucleic acid molecule complementary, or essentially complementary, to the nucleic acid molecule having the sequence set forth in SEQ ID NO:1 or 19. Nucleic acid sequences which are "complementary" are those which are capable of base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment of SEQ ID NO:1 or 19 under relatively stringent conditions such as those described herein in the detailed description of the preferred embodiments. Complementary nucleotide sequences are useful for detection and purification of hybridizing nucleic acid molecules. A preferred embodiment of the invention is a molecule complementary to SEQ ID NO:1 or 19 and is a cDNA molecule complementary to a steroidogenic acute regulatory protein mRNA.

The present inventors also envision the preparation of fusion proteins and peptides, e.g., where the StAR coding regions are aligned within the same expression unit with other proteins or peptides having desired functions, such as for purification or immunodetection purposes (e.g., proteins which may be purified by affinity chromatography and enzyme label coding regions, respectively).

StAR protein has been successfully expressed in eukaryotic expression systems by the present inventors, for example, using the PCMV vector in COS cells. Other expression systems contemplated by the present inventors include, e.g., baculovirus-based, glutamine synthase-based, dihydrofolate reductase-based systems, or the like. For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

Where eukaryotic expression is contemplated, one will also typically desire to incorporate into the transcriptional unit which includes the StAR gene, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

It is contemplated that virtually any of the commonly employed host cells can be used in connection with the expression of StAR in accordance herewith. Examples include cell lines typically employed for eukaryotic expression such as COS, CHO, MA-10 cells, or *Saccharomyces cerevisiae.*

It is proposed that transformation of host cells with DNA segments encoding the StAR protein will provide a convenient means for obtaining purified StAR protein. It is also proposed that cDNA, genomic sequences, and combinations thereof, are suitable for eukaryotic expression, as the host cell will process the genomic transcripts to yield functional mRNA for translation into protein. Other embodiments of the invention comprise compositions comprising a purified RNA molecule corresponding to StAR. Such embodiments, by way of example, have a nucleotide sequence of SEQ ID NO:14, 15, 16, or 17.

Nucleic Acid Hybridization and PCR reactions.

Oligonucleotide sequences based on the mouse or a homologous sequence of StAR may be used as primers in a polymerase chain reaction to screen for possible mutations in StAR mRNA causing a variety of pathologies, for example, the lethal human disease, lipoid congenital adrenal hyperplasia. Therefore, StAR nucleic acid sequence can be applied to screen prenatal, perinatal, or neonatal DNA for possible mutations in StAR. If the disease is detected early, then continual mineralocorticoid, glucocorticoid, or steroid replacement therapy can prolong the life of the patient. Further applications will arise when additional disease states are linked to mutations in the StAR gene, or under conditions where mutations in related genes result in decreased levels of StAR mRNA or protein. In these cases, analysis of StAR mRNA or protein has significant diagnostic value.

DNA probes and primers useful in hybridization studies and PCR reactions may be derived from any portion of SEQ ID NO:1 or 19 and are generally at least about seventeen nucleotides in length. Therefore, probes and primers are specifically contemplated that comprise nucleotides 1 to 17, or 2 to 18, or 3 to 19 and so forth up to a probe comprising the last 17 nucleotides of the nucleotide sequence of SEQ ID NO:1 or 19. Thus, each probe would comprise at least about 17 linear nucleotides of the nucleotide sequence of SEQ ID NO:1 or 19, designated by the formula "n to n+16," where n is an integer from 1 to about 1435. Longer probes that hybridize to the StAR gene under low, medium, medium-high and high stringency conditions are also contemplated, including those that comprise the entire nucleotide sequence of SEQ ID NO:1 or 19. Selected oligonucleotide subportions of the gene encoding StAR have significant utility irrespective of whether they encode antigenic peptides. In these aspects, it is contemplated, for example, that shorter or longer nucleic acid fragments of the StAR gene, prepared synthetically, recombinantly, or otherwise, can be employed as hybridization probes. Such probes can be readily employed in a variety of ways, including their use in the identification of genes encoding StAR in biological tissues or clinical samples, as well as in the detection and evaluation of StAR in pathologies that relate to cholesterol and/or steroid synthesis. Biological or clinical samples include, but are not limited to, biopsy specimens from adrenal or gonadal tissue, or blood, for example.

A general method for preparing oligonucleotides of various lengths and sequences is described by Caracciolo et al. (1989). In general, there are two commonly used solid phase-based approaches to the synthesis of oligonucleotides containing conventional 5'–3' linkages, one involving intermediate phosphoramidites and the other involving intermediate phosphonate linkages. In the phosphoramidite synthesis a suitably protected nucleotide having a cyanoethylphosphoramidate at the position to be coupled is reacted with the free hydroxyl of a growing nucleotide chain derivatized to a solid-support. The reaction yields a cyanoethylphosphite, which linkage must be oxidized to the cyanoethylphosphate at each intermediate step, since the reduced form is unstable to acid.

The phosphonate based synthesis is conducted by the reaction of a suitably protected nucleotide containing a phosphonate moiety at a position to be coupled with a solid phase-derivatized nucleotide chain having a free hydroxyl group, in the presence of a suitable activator to obtain a phosphonate ester linkage, which is stable to acid. Thus, the oxidation to the phosphate or thiophosphate can be conducted at any point during synthesis of the oligonucleotide or after synthesis of the oligonucleotide is complete.

The phosphonates can also be converted to phosphoramidate derivatives by reaction with a primary or secondary amine in the presence of carbon tetrachloride. To indicate the two approaches generically, the incoming nucleotide is regarded as having an "activated" phosphite/phosphate group. In addition to employing commonly used solid phase synthesis techniques, oligonucleotides may also be synthesized using solution phase methods such as triester synthesis. The methods are workable, but in general, less efficient for oligonucleotides of any substantial length.

Preferred oligonucleotides resistant to in vivo hydrolysis may contain a phosphorothioate substitution at each base. Oligodeoxynucleotides or their phosphorothioate analogues may be synthesized using an Applied Biosystem 380B DNA synthesizer (Applied Biosystems, Inc., Foster City, Calif.).

A further embodiment of the invention is a purified nucleic acid molecule having at least a 17, 20, 25, 30, 50, 100, 200, 500, or 1000 nucleotide sequence that corresponds to, or is capable of hybridizing to the nucleic acid sequence of SEQ ID NO:1 or 19 under conditions standard for hybridization fidelity and stability. Furthermore, it is contemplated that nucleic acid molecules having a nucleotide sequence of SEQ ID NOS:1, 9, 10, 11, 12, 13, or 19 for stretches of between about 10 nucleotides to about 20 or to about 30 nucleotides will find particular utility, with even longer sequences, e.g., 40, 50, 150, 250, 450, even up to fill length, being more preferred for certain embodiments. The ability of such nucleic acid probes to specifically hybridize to StAR nucleic acid sequences will enable them to be of use in a variety of embodiments. For example, the probes can be used in a variety of assays for detecting the presence of complementary sequences in a given sample. However, other uses are envisioned, including the use of the sequence information for the preparation of mutant species primers, or primers for use in preparing other genetic constructions.

These probes will be useful in hybridization embodiments, such as Southern and Northern blotting. The total size of fragment, as well as the size of the complementary stretch(es), will ultimately depend on the intended use or application of the particular nucleic acid segment. Smaller fragments will generally find use in hybridization embodiments, wherein the length of the complementary region may be varied, such as between about 20 and about 40 nucleotides, or even up to the full length of the nucleic acid as shown in SEQ ID NOS: 1, 9–13, or 19 according to the complementary sequences one wishes to detect.

The use of a hybridization probe of about 10 nucleotides in length allows the formation of a duplex molecule that is both stable and selective. Molecules having complementary sequences over stretches greater than 10 bases in length are preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,683,202 (herein incorporated by reference) or by introducing selected sequences into recombinant vectors for recombinant production.

Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and\or high temperature conditions, such as provided by 0.02M–0.15M NaCl at temperatures of 50° C. to 70° C. Such selective conditions tolerate little, if any, mismatch between the probe and the template or target strand.

Where one desires to prepare mutants employing a mutant primer strand hybridized to an underlying template or where one seeks to isolate sequences from related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

Longer DNA segments will often find particular utility in the recombinant production of peptides or proteins. DNA segments which encode peptides from about 15 to about 50 amino acids in length, or more preferably, from about 15 to about 30 amino acids in length comprising the amino acid sequence of SEQ ID NO:8 are contemplated to be particularly useful. DNA segments encoding peptides will generally have a minimum coding length in the order of about 45 to about 150, or to about 90 nucleotides. DNA segments encoding full length proteins may have a minimum coding length in the order of about 2000 nucleotides for a protein or otherwise biologically active equivalent peptide having at least a sufficient portion of the sequence in accordance with SEQ ID NO:2 or 18 capable of providing said StAR-biological activity.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol. For example, nucleic acid fragments may be prepared in accordance with the present invention which are up to 10,000 base pairs in length, with segments of 5,000 or 3,000 being preferred and segments of about 1,000 base pairs in length being particularly preferred.

It will be understood that this invention is not limited to the particular nucleic acid and amino acid sequences having sequence identifiers as listed in Table 2. Therefore, DNA segments prepared in accordance with the present invention may also encode biologically functional equivalent proteins or peptides which have variant amino acid sequences. Such sequences may arise as a consequence of codon redundancy and functional equivalency which are known to occur naturally within nucleic acid sequences and the proteins thus encoded. Alternatively, functionally equivalent proteins or peptides may be constructed via the application of recombinant DNA technology, in which changes in the protein structure may be engineered, based on considerations of the properties of the amino acids being exchanged.

Any of a variety of steroidogenic cells may be used as a source to prepare the purified StAR protein of the invention having an amino acid sequence essentially as set forth in SEQ ID NO:2 or sequences having substantial identity thereto. Substantial identity as used in the definition of the present invention is intended to mean amino acid sequences or nucleic acid sequences that have an about 75% to about 99% identical sequence to that of the referenced SEQ ID NO. For example, such a relationship exists between SEQ ID NO:2 (amino acid—mouse) and SEQ ID NO:18 (amino acid—human) and SEQ ID NO:1 (nucleic acid—mouse) and SEQ ID NO:19 (nucleic acid—human). By way of example, particularly useful cells include adrenal fasciculata, adrenal glomerulosa, corpus luteum cells, ovarian theca, ovarian granulosa, mouse Y-1 adrenalcortical tumor cells, primary Leydig cell cultures and MA-10 Leydig tumor cells. The cell line employed to prepare a mitochondrial extract for purposes of isolating the herein described StAR protein may comprise Leydig cell cultures and MA-10 Leydig tumor cells.

Table 2 lists the identity of sequences of the present disclosure having sequence identifiers.

TABLE 2

Identification of Sequences Having Sequence Identifiers

| SEQ ID NO: | IDENTITY |
|---|---|
| 1 | DNA sequence encoding StAR (mouse) |
| 2 | Protein sequence of 30 kDa StAR (mouse) |
| 3 | peptide 23 (mouse) |
| 4 | peptide 25 (mouse) |
| 5 | peptide 45 (mouse) |
| 6 | Asn Gln Glu Gly Trp Lys |
| 7 | Ala Glu His Gly Pro Thr Cys Met Val |
| 8 | amino acids 88–98 of SEQ ID NO:2 (mouse) |
| 9 | degenerate oligonucleotides made to peptide 23; coding direction (mouse) |
| 10 | degenerate oligonucleotides made to peptide 23; noncoding direction (mouse) |
| 11 | degenerate oligonucleotides made to peptide 25; coding direction (mouse) |
| 12 | degenerate oligonucleotides made to peptide 25; noncoding direction (mouse) |
| 13 | PCR product, nucleotides 343–743 of SEQ ID NO:1 (mouse) |
| 14 | RNA sequence encoding StAR (mouse) |
| 15 | RNA sequence encoding StAR peptide (human), (nucleic acid position 267–988 coding region) |
| 16 | RNA sequence encoding StAR peptide (human) (nucleic acid position 127–260 coding region). |
| 17 | RNA sequence for human noncoding StAR region (nucleic acid position 1051–1069). |
| 18 | Amino acid sequence encoding StAR (human) (amino acid 1–285) |
| 19 | DNA sequence encoding StAR (human) |

StAR Protein Compositions

In particular aspects, the present invention provides a purified StAR protein having an amino acid sequence essentially as set forth in SEQ ID NO:2 or 18. In a further embodiment of the composition, the amino acid sequence begins at the amino acid methionine at position 48 of SEQ ID NO: 2 and extends through amino acid cysteine at position 284 of SEQ ID NO:2.

The StAR protein may be phosphorylated or unphosphorylated. The mature 30 kDa form of StAR protein has four different isoelectric species, designated as 30 kDa 1, 2, 3, and 4, with 1 being the most basic form and 4 the most acidic form. Studies by the present inventors demonstrated that forms 3 and 4 were phosphorylated forms of 1 and 2, and that phosphorylation is important for biological activity. These forms of the 30 kDa protein are useful as molecular weight standards, and as standards for isoelectric focusing. Threonine, serine, and tyrosine amino acids are most frequently those amino acids in a protein that are phosphorylated, and in the case of the StAR protein, a threonine may be phosphorylated.

The purified 37 kDa StAR protein is expected to have many different uses, including, for example, supplementing a patient lacking StAR activity to provide proper cholesterol transport and subsequent synthesis of steroids.

In some aspects of the peptides of the StAR protein, the peptides comprise an amino acid sequence in accordance with SEQ ID NO:3, 4, 5, 6, 7, or 8. These peptides are useful for designing oligonucleotides for screening and for identifying antigenic determinants of the StAR protein (see examples). Peptides having less than about 45 amino acid residues may be chemically synthesized by the solid phase method of Merrifield (1963), which reference is specifically incorporated by reference herein, using an automatic peptide synthesizer with standard t-butoxycarbonyl (t-Boc) chemistry that is well known to one skilled in this art in light of this disclosure. The amino acid composition of the synthesized peptides may be determined by amino acid analysis with an automated amino acid analyzer to confirm that they correspond to the expected compositions. The purity of the peptides may be determined by sequence analysis or HPLC.

In still another embodiment of the present invention, methods of preparing a StAR protein composition are provided. In one aspect, the method comprises growing recombinant host cells comprising a vector that encodes a protein which includes an amino acid sequence in accordance with SEQ ID NO:2 or 18, or that includes a nucleic acid sequence as defined in SEQ ID NO: 1 or SEQ ID NO: 19, under conditions permitting nucleic acid expression and protein production followed by recovering the protein so produced. The host cell, conditions permitting nucleic acid expression, protein production and recovery, will be known to those of skill in the art, in light of the present disclosure of the StAR gene. A preferred host cell is a COS cell.

Modifications and changes may be made in the sequence of the StAR peptides or protein of the present invention and still obtain a peptide or protein having like or otherwise desirable characteristics. For example, certain amino acids may be substituted for other amino acids in a peptide without appreciable loss of function. Since it is the interactive capacity and nature of an amino acid sequence that defines the peptide's functional activity, certain amino acid sequences may be chosen (or, of course, its underlying DNA coding sequence) and nevertheless obtain a peptide with like properties. It is thus contemplated by the inventors that certain changes may be made in the sequence of a StAR peptide or protein (or underlying DNA) without appreciable loss of its ability to function.

Substitution of like amino acids can be made on the basis of hydrophilicity. U.S. Pat. No. 4,554,101, incorporated herein by reference, states that the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent peptide. In such changes, the substitution of amino acids whose hydrophilicity values are within ±2 is preferred, those which are within ±1 are more preferred, and those within ±0.5 are most preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threomine; glutamine and asparagine; and valine, leucine and isoleucine.

Two designations for amino acids are used interchangeably throughout this application, as is common practice in the art. Alanine=Ala (A); Arginine=Arg (R); Aspartate=Asp (D); Asparagine=Asn (N); Cysteine=Cys (C); Glutamate=Glu (E); Glutamine=Gln (Q); Glycine=Gly (G); Histidine=His (H); Isoleucine=Ile (1); Leucine=Leu (L); Lysine=Lys (K); Methionine=Met (M; Phenylalanine=Phe (F); Proline=Pro (P); Serine=Ser (S); Threonine=Thr (T); Tryptophan=Trp (W); Tyrosine=Tyr (Y); Valine=Val (V).

While discussion has focused on functionally equivalent polypeptides arising from amino acid changes, it will be appreciated that these changes may be effected by alteration of the encoding DNA, taking into consideration also that the genetic code is degenerate and that two or more codons may code for the same amino acid.

Another aspect of the invention is a method of preparing a recombinant steroidogenic acute regulatory protein encoded by the purified nucleic acid molecule having a nucleotide sequence of SEQ ID NO:1 or 19, the method comprising the steps of preparing a recombinant host bearing the nucleic acid molecule, the host being capable of expressing the protein, culturing the recombinant host to produce steroidogenic acute regulatory protein, and collecting the recombinant steroidogenic acute regulatory protein having an amino acid sequence essentially as set forth in SEQ ID NO:2 or 18. In one aspect, the recombinant host is a COS cell.

A further embodiment of the present invention relates to a purified nucleic acid molecule encoding StAR protein having an amino acid sequence essentially as set forth in SEQ ID NO: 2, said nucleic acid molecule obtained by a process of; i) preparing oligonucleotides that encode a segment of an amino acid sequence of SEQ ID NO:2 and that have at least about 17 nucleotides; ii) screening an animal cell DNA library with said oligonucleotides; and iii) obtaining the purified nucleic acid molecule encoding StAR protein having an amino acid sequence essentially as set forth in SEQ ID NO: 2 or 18.

Pharmaceutical Preparations

Another aspect of the present invention provides therapeutic agents for the treatment of steroid hormone-dependent disorders in an animal. The therapeutic agent comprises an admixture of StAR peptide or protein in a pharmaceutically acceptable excipient. Most preferably, the therapeutic agent will be formulated so as to be suitable for injection. Pharmacologically active peptides of StAR may also be provided to a subject via gene therapy. Many different vehicles exist for accomplishing this end, such as incorporation of the StAR gene, or fragment thereof, into an adenovirus, retrovirus, or other techniques known to those of skill in the art in light of the present disclosure. Ex vivo gene therapy is also contemplated as another mode of administration.

Such preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The active compounds may be administered parenterally or intrapertoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged adsorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. See, for example, Remington (1995), which reference is incorporated by reference herein.

Antibodies

In another aspect, the present invention includes an antibody that is immunoreactive with a StAR polypeptide as described for the invention. An antibody can be a polyclonal or a monoclonal antibody. In some embodiments, the antibody is a monoclonal antibody. In addition, the antibodies may comprise recombinant antibodies and may be obtained employing the information provided here on StAR in conjunction with those techniques well know to those of skill in the art. These antibodies may further be described as chimeric recombinant antibodies, particularly humanized chimeric antibodies specific for StAR. Means for preparing and characterizing antibodies are well known in the art (See, e.g., *Antibodies "A Laboratory Manual,* E. Howell and D. Lane, Cold Spring Harbor Laboratory, 1988). A preferred polyclonal antibody has binding specificity for amino acids 1-26, 10-26, 36-47, or 88-98 of SEQ ID NO:2.

In addition, the antibodies may comprise recombinant antibodies, and may be obtained employing the information provided here on StAR in conjunction with those techniques well known to those of skill in the art. These antibodies may further be described as chimeric recombinant antibodies, particularly humanized chimeric antibodies specific for StAR. See, for example, Munro (1984) *Nature* 312:597; U.S. Pat. No. 5,225,599.

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

Antibodies, both polyclonal and monoclonal, specific for the peptides of the present invention may be prepared using conventional immunization techniques, as will be generally known to those of skill in the art. A composition containing antigenic epitopes of the peptide sequences, isolated peptides, or fragments thereof can be used to immunize one or more experimental animals, such as a rabbit or mouse, which will then proceed to produce specific antibodies against StAR. Polycolonal antisera may be obtained, after allowing time for antibody generation, simply by bleeding the animal and preparing serum samples from the whole blood.

In one embodiment, the polyclonal antibodies to StAR were prepared by injecting a rabbit with a StAR peptide 88-98 (SEQ ID NO:8) conjugated to KLH (keyhole limpet hemocyanin) mixed with a StAR peptide 88-98 modified according to the MAP procedure (with a branched lysine core) (See Tam et al (1989) *J. of Immun. Methods,* 123:53–61) incorporated herein by reference. Prior attempts to raise antibody using as immunogen the mouse StAR peptide, 97-107 was less successfully generating antibody.

To obtain monoclonal antibodies, one would also initially immunize an experimental animal, often preferably a mouse, with a purified peptide composition. One would then, after a period of time sufficient to allow antibody generation, obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to the desired peptide.

Following immunization, spleen cells are removed and fused, using a standard fusion protocol (see, e.g., The Cold Spring Harbor Manual for Hybridoma Development, incorporated herein by reference) with plasmacytoma cells to produce hybridomas secreting monoclonal antibodies against the desired peptide. Hybridomas which produce monoclonal antibodies to the selected antigens are identified using standard techniques, such as ELISA and Western blot methods.

Hybridoma clones can then be cultured in liquid media and the culture supernatants purified to provide the peptide-specific monoclonal antibodies. In general, monoclonal antibodies to the peptide antigen can be used in the identification of steroid hormone-dependent disorders. It is proposed that the monoclonal antibodies of the present invention will find useful application in standard immunochemical procedures, such as ELISA and Western blot methods, as well as other procedures which may utilize antibody specific to common or allelically distinct peptide epitopes.

Monoclonal and polyclonal antibodies raised against peptides or protein of the present examples as useful for (1) screening a cDNA expression library in the process of cloning a gene that encodes a particular protein or related protein (for example, the SUPERSCREEN® immunoscreening system from AMERSHAM®), (2) facilitating the purification of a particular protein or related protein by using column chromatography to which the monoclonal antibody is bound, and (3) providing reagents necessary for a diagnostic immunoassay for screening biological samples.

Monoclonal antibodies are obtained using the following procedure:

Immunization Schedule for Raising Monoclonal Antibodies

1. For each mouse, mix 250 μl of antigen solution containing 10 μg of antigen with 250 μl of complete Freund's adjuvant. Inject six BALB/c female mice ip (intraperitoneal injection).
2. After 14 days, repeat the injections of antigen and incomplete Freund's adjuvant.
3. Collect tail bleeds from immunized mice on day 24. Do 1 in 5 dilutions in phosphate buffered saline (PBS) and test all samples by comparison with similar dilutions of normal mouse serum in a dot blot.
4. On day 35, inject all animal ip with antigen and incomplete Freund's.
5. Day 45, do tail bleeds and test by dot blot. All serum samples checked by immunoprecipitation against in vivo radiolabeled antigen preparation.
6. Day 56, inject best responder, 100 μl iv and 100 μl ip. All others get ip injection with incomplete Freund's.
7. Day 59, fuse splenocytes from best responder.

In still another embodiment of the invention, a hybridoma cell line which produces a monoclonal antibody which specifically binds StAR protein is provided. Most particularly, the hybridoma cell line is an animal hybridoma cell line prepared by a process of immunizing an animal, such as a mouse or a rat, with StAR protein, isolating anti-StAR antibody producing cells from the immunized animal, and fusing the antibody producing cells with a neo-plastic animal cell line to obtain a hybridoma cell line. The resultant hybridoma tissue culture supernatants are screened for monoclonal antibodies as follows:

1. A protein solution of at least 1 μg/ml of antigen is added to a nitrocellulose sheet at 0.1 ml/cm$^2$. Allow the protein to bind to the paper for 1 hr. Higher concentrations of proteins will increase the signal and make screening faster and easier. If the amount of protein is not limiting, concentrations of 10–50 μg/ml should be used. Nitrocellulose can bind approximately 100 μg of protein per cm$^2$.
2. Wash the nitrocellulose sheet three times in PBS.
3. Place the sheet in a solution of 3% BSA in PBS with 0.02% sodium azide for 2 hr to overnight. To store the sheet, wash twice in PBS and place at 4° C. with 0.02% sodium azide. For long-term storage, shake off excessive moisture from the sheet, cover in plastic wrap, and store at −70° C.
4. Place the wet sheet on a piece of parafilm, and rule with a soft lead pencil in 3-mm squares. Cut of enough paper for the number of assays.
5. Apply 1 μl of the hybridoma tissue culture supernatant to each square. Incubate the nitrocellulose sheet on the parafilm at room temperature in a humid atmosphere for 30 min.

Along with dilutions of normal mouse serum, include dilutions of the mouse serum from the last test bleed as controls. Dilutions of the test sera are essential to control correctly for the strength of the positive signals. Mouse sera will often contain numerous antibodies to different regions of the antigen and therefore will give a stronger signal than a monoclonal antibody. Therefore, dilutions need to be used to lower the signal. Good monoclonal antibodies will appear 10-fold less potent than good polyclonal sera.

6. Quickly wash the sheet three times with PBS, then wash two times for 5 min each with PBS.
7. Add 50,000 cpm of $^{125}$I-labeled rabbit anti-mouse immunoglobulin per 3-mm square in 3% BSA/PBS with 0.02% sodium azide (about 2.0 ml/cm$^2$).
8. After 30–60 min of incubation with shaking at room temperature, wash extensively with PBS until counts in the wash buffer approach background levels.
9. Cover in plastic wrap and expose to X-ray film with a screen at −70° C.

The hybridoma identified as producing antibody to the protein of interest is passaged as follows:

1. Inject $10^7$ (or less) cells into female mice that have been injected ip about 1 week earlier with 0.5 ml of pristane or incomplete Freund's adjuvant. These types of injections are also used in prime mice for ascites production, and this may serve as a convenient source of appropriate hosts. If no mice are available, inject mice with incomplete Freund's adjuvant and wait 4 hr to 1 day before injecting the hybridoma cells. The animals must be of the same genetic background as the cell line.
2. If an ascites develops, tap the fluid and transfer into a sterile centrifuge tube.
3. Spin the ascites at 400 g for 5 min at room temperature.
4. Remove the supernatant. Resuspend the cell pellet in 10 ml of medium supplemented with 10% fetal bovine serum and transfer to a tissue culture plate. The supernatant can be checked for the presence of the antibody and used for further work if needed.
5. Handle as for normal hybridomas, except keep the cells separate from the other cultures until there is little chance of the contamination reappearing.

The present invention is still another aspect defines an immunoassay for the detection of a StAR protein in a biological sample. In one particular embodiment of the immunoassay, the immunoassay comprises; preparing an antibody having binding specificity for StAR protein to provide an anti-StAR antibody, incubating the anti-StAR antibody with the biological sample for a sufficient time to permit binding between antibody and StAR present in said biological sample, and determining the presence of bound antibody by contacting the incubate of the sample and antibody with a detectably labeled antibody specific for the anti-StAR antibody, wherein the presence of anti-StAR antibody in the biological sample is detectable as the measure of the detectably labeled antibody from the biological sample. In some embodiments, the antibody is preferably a monoclonal antibody having binding specificity for the StAR amino acid sequence 88-98 of SEQ ID NO:2 or a region of identical amino acid sequence in SEQ ID NO. 18(See (FIG. 5).

By way of example, the antibody may be labeled with any of a variety of detectable molecular labeling tags. Such include, an enzyme-linked antibody, a fluorescent-tagged antibody, or a radio-labelled antibody.

A further embodiment of the invention is a method for detecting a chromosomal genetic lesion comprising the steps of i) preparing a nucleic acid probe having nucleotide sequence that includes at least a 17-base segment of SEQ ID NO:1 or 19 corresponding to a region of a StAR genetic lesion in a diseased patient sample; corresponding to a region of a StAR genetic lesion in a diseased patient sample; ii) contacting a chromosomal angle with the probe to allow hybridization of the sample to the probe under conditions standard for hybridization fidelity and stability, wherein lack of specific hybridization of the probe and the chromosomal sample provides for detection of a potential genetic lesion in the chromosome. The genetic lesion may be a deletion, a rearrangement, an insertion, a transition, a transversion, a frameshift, a missense or a nonsense mutation. In particular, the genetic lesion correlates with the presence of lipid congenital adrenal hyperplasia. Human tissue samples may be biopsy material from adrenal tissue, gonadal tissue, or blood.

In another aspect of the invention, a screening method for lipid congenital adrenal hyperplasia is provided. The method comprises the steps of i) obtaining a chromosomal sample to provide a test sample ii) preparing a nucleic acid probe having a nucleotide sequence essentially as set forth in SEQ ID NO:1 or 19; and, iii) contacting the test sample with the nucleic acid probe under hybridization conditions allowing for detection of a mismatch in a hybridizing molecule as a screening method for lipid congenital adrenal hyperplasia. A mismatch is determined most readily by determining the nucleotide sequence of the hybridizing molecule, a difference in the nucleotide sequence of the hybridizing molecule and the nucleotide sequence of SEQ ID NO:1 and 19 provides a screen for lipid congenital adrenal hyperplasia.

Further embodiments of the invention include; a method for stimulating choleterol transport, a method for increasing production of progesterone, and a method for increasing steroidogenesis; these methods comprise administering a pharmacologically effective amount of steroidogenic acute regulatory protein having an amino acid sequence essentially as set forth in SEQ ID NO:2 or 18. Progesterone is used clinically in a variety of applications in males and females. Methods for providing enhanced production of progesterone are thus a valuable application of the StAR compositions of the present invention. The protein may be delivered by recombinant means, i.e., synthesis from an expression vector containing nucleic acid sequences encoding the protein.

Following long-standing patent law convention, the terms "a" and "an" mean one or more" when used in this application, including the claims.

| Abbreviations | |
|---|---|
| $Bt_2cAMP$ | $N^6$, 2'-O-dibutyryladenosine-3':5'-cyclic monophosphate |
| CHAPS | 3-[3-cholamidopropyl dimethylammonio] 1-propanesulfonate |
| CSCC | cholesterol side-chain cleavage |
| DBI | diazepam binding inhibitor |
| hCG | human chorionic gonadotropin |
| HPLC | high performance liquid chromatography |
| IOD | integrated optical density |
| LH | luteinizing hormone |
| Mops | 3-[N-Morpholino]propane-sulfonic acid |
| PAGE | polyacrylamide gel electrophoresis |
| PBR | peripheral benzodiazepine receptor |
| PBS | Dulbecco's phosphate-buffered saline with calcium and magnesium |
| PCR | polymerase chain reaction |
| SAP | steroidogenesis activator polypeptide |
| $SCP_2$ | sterol carrier protein 2 |
| WAY | Waymouth's MB 752 media |

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2. Nucleotide sequence of the 37 kDa cDNA clone (SEQ ID NO:1) and the deduced amino acid sequence for the protein SEQ ID NO:2). The nucleotides are numbered to the left with position 1 as the first nucleotide in the cDNA and the amino acid are numbered to the right with amino acid 1 being the initiating methionine of the mitochondrial precursor. Capital letters are used for the coding region of the cDNA and to denote the in-frame stop codon in the 5' untranslated region and the polyadenylation signal and poly $(A)^+$ tail in the 3' untranslated region. The amino acids corresponding to peptides 23, 25, and 45 are underlined and the corresponding peptide is indicated below the line. The underlined nucleotide sequences were included in the set of degenerate oligonucleotides designed from the amino acid sequence. The antibody was raised against amino acids 88-98 which includes most of peptide 25. The mature protein beings with the methione at position 48 (see Example 2 regarding cleavage of the precursor protein).

FIG. 3. Nucleic acid sequence of human StAR and mouse StAR. Segments of high identity of nucleic acid sequence are shown.

FIG. 5. Comparison of the deduced amino acid sequences from known nucleotide sequences of the putative coding region of StAR protein from mouse, human, bovine and ovine. Only a partial sequence is presented for ovine. Putative conserved phosphorylation sites that correspond to consensus motifs are highlighted for PKA and CAM kinase II (A), PKC (C), CKII (CK), and P34CDC2 kinase (CD). The proposed cleavage sites for the mitochondrial proteases, matrix-processing protease, and mitochondrial intermediate-processing peptide are noted (C1 and C2); however, only the mouse sequence strictly follows the consensus motif for two cleavages with the other sequences predicting one cleavage. Another putative PKA phosphorylation site is found in bovine and human sequences at position 277. While Ser 277 is not conserved in the murine sequence, there is a Ser at 278. If phosphorylation is crucial to the function of StAR protein and this Ser is the residue that is phosphorylated, then this may explain how the C-terminal deletion mutants found in lipoid CH patients affect StAR function.

DETAILED DESCRIPTION OF THE PREFERRED EMBODIMENTS

Figure 1:
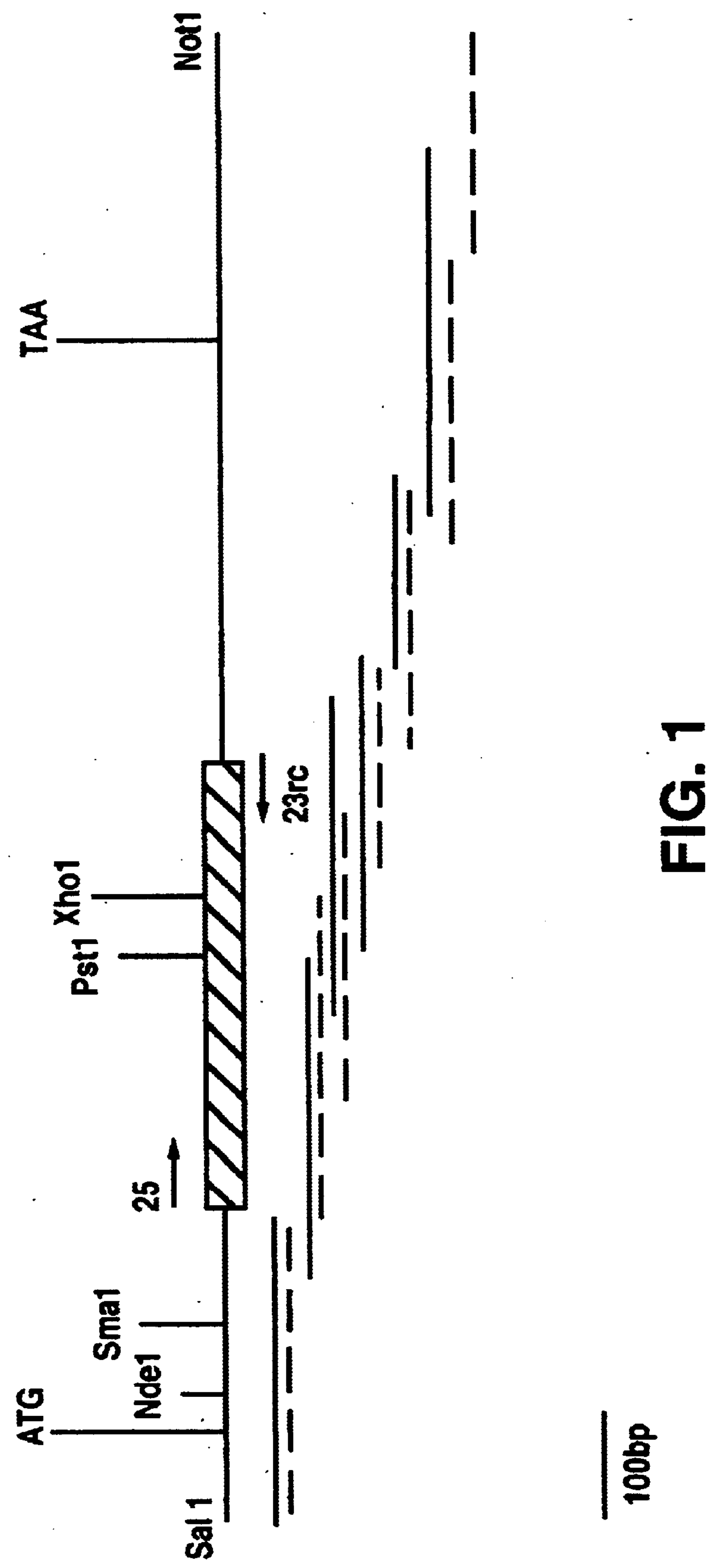
FIG. 1. Restriction map of the isolated cDNA clone encoding the 37 kDa precursor protein. The initiating ATG codon and the termination codon, TAA, are indicated by vertical bars along with several unique endonuclease restriction sites. The arrowheads indicate the position of the degenerate oligonucleotides designed from peptides 25 and 23, and the hatched bar denotes the region amplified by PCR using these oligonucleotides. The PCR amplified product was used to screen the cDNA library. Both the coding and noncoding strand of the cDNA were sequenced. The solid lines shown beneath the map represent the overlapping fragments of the coding strand which were sequenced while the dashed lines represent the noncoding strand fragments which were sequenced by the dideoxynucleotide sequencing method of the Sanger et al. (1977) using the Sequenase Version 2 kit (United States Biochemical).
Figure 4:
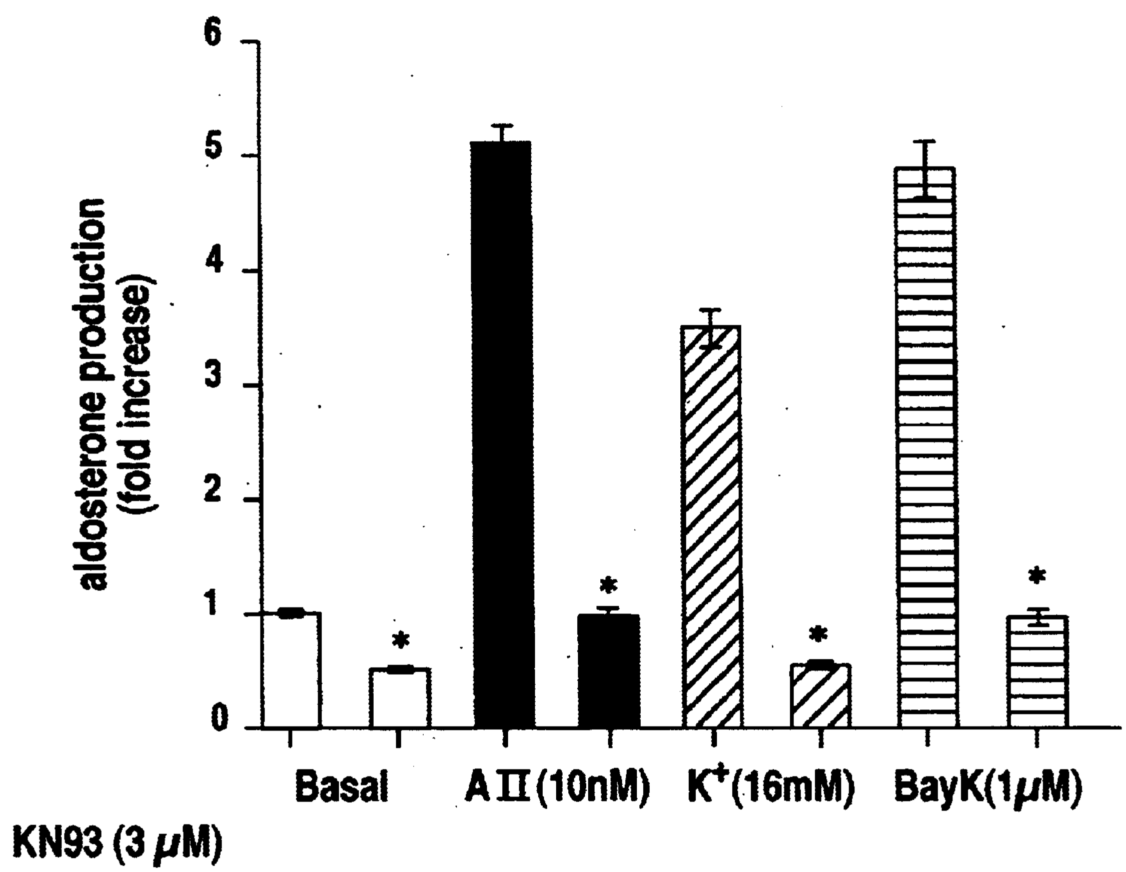
FIG. 4. Effect of KN93 on agonist-stimulated aldosterone production and StAR protein expression in H295R cells. Cells were incubated for six hours with Ang II (100 nM), K+(16 $\mu$M), and Bay K(1 $\mu$M) in the presence or absence of KN93 (3 $\mu$m). The medium aldosterone content was determined by R.I.A. and normalized to the tissue culture well protein content. Data points represent the mean ±SE of values from six separate culture wells expressed as fold increase over basal. Significant inhibition relative to the control response is indicated at *$p<0.01$. StAR protein was examined using equivalent amounts of total cellular lysate (30 $\mu$g) by immunoblot analysis as described in the Methods. Results are representative of those obtained from three separate experiments.

The present inventors have utilized the MA-10 mouse Leydig tumor cell line to study the acute regulation of steroidogenesis. Specifically, the inventors have identified a family of hormone-induced mitochondrial proteins in MA-10 cells that regulate cholesterol delivery to the inner mitochondrial membrane and the CSCC. These proteins have been described as the mitochondrial 37 kDa, 32 kDa, and 30 kDa molecular weight proteins and they are synthesized in response to either LH and HCG or by stimulation with the CAMP analogue, $Bt_2cAMP$. The 30 kDa species consists of four separate proteins and proteolytic digestion of all four forms indicates that they are all modified forms of the same protein. Pulse chase experiments and tryptic peptide mapping of the 37 kDa and 30 kDa proteins indicated that the 37 kDa form is a precursor to the 30 kDa protein.

The following data support the involvement of these proteins in the acute regulation of steroidogenesis: i) the synthesis is directly correlated to the capacity of the MA-10 cells to produce steroid in response to hormone stimulation in both a time and dose responsive manner; ii) their synthesis is sensitive to cycloheximide; iii) the 30 kDa proteins are localized to the mitochondria and are processed from a larger precursor protein of 37 kDa; iv) a rat Leydig tumor cell line ($R_2C$) which constitutively produces steroids constitutively expresses the 30 kDa proteins; and v) inhibition of steroidogenesis is concomitant with inhibition of synthesis of 30 kDa proteins (Stocco and Kilgore, 1988; Stocco and Chaudhary, 1990; Stocco and Chen, 1991; Stocco and Sodeman, 1991; Stocco, 1992; Stocco and Ascoli, 1993; Stocco et al., 1993; Stocco and Clark, 1993).

The present inventors have now cloned the cDNA for this family of proteins, and have also more directly determined their function in the regulation of steroid production, particularly in MA-10 cells.

The following examples describe the purification of the MA-10 30 kDa proteins and the isolation and characterization of a full length cDNA clone. The cDNA encodes a novel mouse protein of 31.6 kDa, which relates to the previously described 37 kDa precursor protein of the LH-induced family of mitochondrial proteins. The amino acid sequence at the amino terminus has been identified by the present inventors to be characteristic of a mitochondrial targeting signal. Using an in vitro transcription/translation system, the precursor protein was processed and modified to all forms of the 30 kDa proteins by isolated mitochondria. Immunoblot analysis of mitochondria isolated from either $Bt_2cAMP$-stimulated MA-10 cells or MA-10 cells transfected with the cDNA confirmed the cDNA encodes the same immunospecific 30 kDa protein. In addition, in the absence of hormone stimulation, expression of the 30 kDa protein in MA-10 cells resulted in a 1.5–3.5 increase in progesterone production above cells transfected with vector alone. Thus, the present inventors have demonstrated for the first time that expression of the LH-inducible 30 kDa protein directly results in an increase in steroid biosynthesis. This protein is required in the acute regulation of hormone-induced steroidogenesis.

Materials & Methods. The materials and methods used in the following examples are provided here. In light of these teachings, one of skill in the art would realize that other equivalent materials and methods may be used in the present invention.

Chemicals. Waymouth's MB 752 medium, Dulbecco's modified Eagle's medium, horse serum, fetal bovine serum, antibiotics and PBS were purchased from Life Technologies, Inc. (Gaithersburg, Md.). $Bt_2cAMP$, leupeptin, aprotinin, pheylmethylsulfonyl fluoride, formaldehyde, and *Escherichia coli* alkaline phosphatase were obtained from Sigma (St. Louis, Mo.). Silver nitrate was from Fisher (Houston, Tex.). The ampholines and stock solutions of nucleic acids were purchased from Pharmacia Biotech Inc. (Piscataway, N.J.). Restriction endonucleases, T7 RNA polymerase, RNAsin, and Taq DNA polymerase were purchased from Promega (Madison, Wis.). Radiolabeled nucleotides [$^{32}$-P] CTP and [$^{25}$S]-methione were obtained from Du Pont NEN (Boston, Mass.). Oligonucleotides were synthesized and purified by Midland Certified Reagent Co. (Midland, Tex.).

Maintenance of MA-10 and COS 1 cells. The MA-10 mouse Leydig tumor cell line was from Dr. M. Asocli (Dept. of Pharmacology, Univ. of Iowa College of Medicine, Iowa City, Iowa). These cells were derived from the M5480P tumor, they have functional LH/CG receptors and produce large amounts of progesterone rather than testosterone in response to hormone stimulation. The cells were grown in Waymouth's MB/752 media containing 15% horse serum ($WAY^+$) at 37° C. in a humid atmosphere under 5% $CO_2$ and maintained in culture using standard techniques (Asocli, 1981). COS 1 cells were obtained from the America Type Culture Collection (#CRL 1650) and grown in Dulbecco's modified Eagle's medium high glucose media containing 10% fatal bovine serum and 100 units of penicillin/ml and 10 units of streptomycin sulfate/ml.

Isolation of Mitochondria. MA-10 cells were stimulated for 6 h with 1 mM $Bt_2cAMP$ in Waymouth's media containing 5% horse serum, then washed once with PBS (Life Technologies, Inc.) and collected in 0.25 M sucrose, 10 mM Tris, pH 7.4, 0.1 mM EDTA by scraping with a rubber policeman. The cells were lysed by homogenization at 1000 rpm for 25 passes with a Potter Elvehjem homogenizer fitted with a serrated Teflon pestle. The homogenate was centrifuged at 600×g for 30 min, and the resultant supernatant was centrifuged at 9000×g for 30 min to pellet the mitochondria. The mictochondrial pellets were stored frozen at −80° C. until used to purify the 30-kDa proteins.

For the in vitro translation reactions, mitochondria were isolated as above with the following exceptions; MA-10 cells were not stimulated with hormone, and the cells were lysed using a glass-on-glass Dounce homogenizer with fitted pestle and homogenized by hand for 25 passes. The mitochondrial pellet was washed once with import buffer (3% bovine serum albumin, 70 mM KCl, 220 mM sucrose, 10 mM Mops/KOH (pH 7.2), 2.5 mM $MgCl_2$ (Hartl, 1986) then resuspended in 200 μl of the import buffer to a protein concentration of 7.5 mg/ml. Mitochondria were used immediately after isolation for the in vitro translation reaction. Isolation of mitochondria from COS 1 cells for immunoblot analysis was as described (Clark and Waterman, 1991).

Purification of the 30-kDa Proteins from Isolated Mitochondria. In general, mitoplasts (mitochondria stripped of outer membrane) were purified from isolated mitochondria and solubilized with CHAPS detergent. Preparative one-dimensional SDS-PAGE gels were used to isolate CHAPS soluble proteins of 28–32 kDa in size (30-kDA fraction), and the 30-kDa proteins were isolated and recovered by two-dimensional SDS-PAGE of the 30 kDa fraction. A more detailed description of this purification is as follows. p Preparation of Mitoplasts and CHAPS Solubilization. Mitroplasts were prepared using the methods detailed by Ardail et al. (1991). Mitochondria were resuspended in swelling buffer (10 mM) potassium phosphate, pH 7.4, 0.1 mM EDTA, 1 mM phenylmethylsulfonyl fluoride, 0.1 mg leupeptin/ml, and 0.04 units approtinin/ml) to a protein concentration of 2.5 mg/ml, incubated on ice for 20 min, then homogenized 5 times by hand using a glass Dounce homogenizer fitted with a Teflon pestle. An equal volume of swelling buffer containing 30% sucrose was added to the shocked mitochondria and mixed thoroughly, Mitoplasts were recovered by centrifugation at 12,000×g for 30 min, resuspended in swelling buffer to a protein concentration of 2.5 mg/ml, and solubilized by adding a fresh solution of swelling buffer containing 25% CHAPS to achieve a 1:1 mg protein to mg detergent ratio (0.25% CHAPS final concentration). The CHAPS soluble sample was recovered after a 100,000×g centrifugation for 45 min and concentrated under nitrogen pressure using a Filtron stir-cell with 10,000 molecular weight cut off (Pharmacia Biotech Inc.). Protein was determined for each fraction by the method of Bradford (1976).

Preparative One-dimensional SDS-Polyacrylamide Gel Electrophoresis. The CHAPS soluble sample was separated on a preparative 1.5 mm 12.5% SDS-polyacrylamide gel (Laemmli, 1970). A 5 mm section of the polyacrylamide gel corresponding to 28–32 kDa band was excised, and the proteins were electroeluted from the gel and concentrated using the Centrilutor micorelectroeluter system (Amicon). The position of the 5 mm strip was determined by running a reference lane containing molecular weight markers and cutting the lane from the gel and staining the markers with Coomassie blue.

Two-Dimensional Polyacrylamide Gel Electrophoresis. Approximately 150–250 μg of the 30 kDa fraction (the concentrated 28–32 kDa proteins from the one-dimensional gel) was resolved by two-dimensional PAGE (O'Farrell, 1975), and the proteins were electrophoretically transferred to nitrocellulose in 20 mM Tris/Cl pH 7.4, 150 mM glycine, 10% β-mercaptoethanol, 0.01% SDS for 4 h at 350 mA (Deutscher, 1990; Towbin, et al. 1979). The nitrocellulose was transiently stained with Ponseau S (0.2% in 1% acetic acid) to visualize and isolate the specific 30 kDa proteins for subsequent amino acid microsequence analysis. The filters were destained with 1% acetic acid, and washed thoroughly with HPLC grade water. The nitrocellulose spots were stored damp at −80° C. until shipped to the Harvard Microchemical facility where the in situ digestion, peptide separation, and microsequence analysis was performed on a fee-for service basis.

Quantitation of Silver Stained Proteins. The two-dimensional SDS-PAGE gels were fixed in 50% methanol, 12% acetic acid for 1 h, then washed with 50% EtOH 3 times for 20 min with each wash. To silver strain the proteins, the gel was pretreated with 0.02% sodium thiosulfate for 1 min, rinsed 3 times with $H_2O$ for 20 s each rinse, then treated with 0.2% silver filtrate, 0.02% formaldehyde for 20 min. After the silver nitrate impregnation, the gel was rinsed with $H_2O$ twice and developed with 6% sodium carbonate, 0.02% formaldehyde. The silver-stained image was captured, and the integrated optical densities (IOD) of the proteins were quantitated using the BioImage Visage 2000 computer-assigned image analysis system (BioImage, Ann Arbor, Mich.). The percent of the total IOD of each spot (protein) was determined automatically and used to quantitate the 30-kDa protein. For example, the percent of total IOD for 30-kDa protein 1×mg total protein loaded onto the first dimension gel/mg total protein for the fraction=mg 30-kDa protein 1 in that fraction.

Preparation of the $Bt_2$cAMP-stimulated MA-10 Mouse Leydig Tumor Cell cDNA library. Total RNA was isolated from 6-h $Bt_2$cAMP-stimulated MA-10 cells by a one-step extraction adapted from the methods of Chomczynski and Sacchi (1987) using RNA STAT-60 (Tel-Test B, Inc., Friendswood, Tex.). Poly $A^+$ mRNA was twice selected on a gravity flow oligo-dT column (5-Prime-3 Prime, Inc.). A λgt22A cDNA library was constructed from the poly$A^+$ RNA using the SuperScript Lambda for cDNA synthesis and λ cloning (Life Technologies, Inc.). Briefly, first strand synthesis was generated using a NotI Primer-Adapter and SuperScript RT, an engineered Moloney murine leukemia virus reverse transcriptase. Second strand synthesis was generated by nick translation replacement of the template mRNA and as Sal/I adapter was ligated to the cDNA ends. The cDNAs were digested with NotI and SalI restriction enzymes and cloned into λgt22A. The DNA was packaged in vitro using the λ Packaging System (Life Technologies, Inc.) and the recombinant phages were stored in 50 mM Tris/Cl pH 7.5, 100 mM NaCl, 1 mM $MgSO_4$, 0.01% gelatin $CHCl_2$ at 4° C. The cDNA library contained $9\times10^3$ independent clones. The *E. coli* strain Y1090r (Life Technologies, Inc.) was infected with the stock phage solution, and the library was amplified to a titer of $2\times10^{10}$ plaque-forming units/ml before the initial screen.

Cloning the 30kDa cDNA. Standard methods were used to purify bacteriophage λ particle from the amplified cDNA library and to extract the recombinant DNAs (Sambrook, et al., 1989). Degenerative oligonucleotides were designed based on the amino acid sequences from peptide 23 and peptide 25 and used for primer-directed amplification of the DNA isolated from the library. Since the position of the peptides relative to each other within the protein was not known, both the coding and reverse complement sequences were synthesized. The coding and reverse complement sequences for peptide 23 used were 5'-GCN GAR CAY GGN CCN ACN TGY ATG G-3' (SEQ ID NO:9) and 5'-C CAT RCA NGT NGG NCC RTG YTC NGC-3' (SEQ ID NO:10), respectively, and for peptide 25 were 5'-AAY CAR CAR GGN TGG AA-3' (SEQ ID NO:11) and 5'-TTC CAN CCY TCY TGR TT-3' (SEQ ID NO:12), respectively. In these designations, N is inosine, R is A or G, Y is T or C. The corresponding sequences are underlined in FIG. 2. The oligonucleotides were synthesized and purified by HPLC by Midland Certified Reagent Co. (Midland, Tex.). Conditions for amplification of the DNA by the polymerase chain reaction were 20 mM Tris/Cl pH 8.4, 50 mM KCl, 2.5 mM $MgCl_2$, 0.1 mg/ml bovine serum albumin, 10 mM concentration of each dATP, dCTP, dTTP, dGTP, 50 pmol of each primer, 2.5 units Taq DNA polymerase, and 1 μg cDNA (Saiki, et al., 1988). Thirty cycles of amplification were performed at 92° C. for 1 min, 45° C. for 30 s, and 72° C. for 30 s. A specific PCR product of 400 base pairs was amplified from the isolated cDNAs and subcloned into the Sma1 site of Bluescript KS (Stratagene, La Jolla, Calif.). An [$\alpha^{32}$P-]-CTP-labeled riboprobe was synthesized and used to screen the cDNA library. Solution hybridization and stringent washing was performed using standard procedures (Sambrook, et al., 1989). One positive clone was plaque-purified from an initial screen of $1\times10^6$ clones. The cDNA was directionally subcloned into the prokaryotic expression vector, pSPORT 1 (Life Technologies, Inc.), using the SalI and NotI cloning sites. A series of nested deletions were constructed (Erase-A-Base kit, Promega, Madison, Wis.) to generate overlapping clones from both the 5' and 3' ends of the cDNA. Both strands of the cDNA were sequenced by the dideoxynucleotide sequencing method of Sanger using the Sequenase Kit Version 2 (United States Biochemical Corp., Cleveland, Ohio) (Sanger, et al., 1977). Electrophoresis was performed in an 8% polyacrylamide gel (Hydrolink, AT Biochem. Malvern, Pa.) with 8 M urea and 25% formamide (v/v). The regions sequenced are indicated in FIG. 1.

In vitro Transcription/Translation of the Cloned cDNA. NotI linearized pSPORT 1/cDNA template (2.5 μg) was transcribed in a 100 μl reaction containing 40 mM Tris/Cl (pH 7.5), 6 mM $MgCl_2$ mM spermidine, 10 mM NaCl, 10 mM dithiothreitol, 100 units RNAsin, 0.5 mM of each UTP, CTP, GTP, ATP, and 40 units T7 RNA polymerase for 2 h at 37° C. In vitro translation reactions were performed in parallel and included either 15 82 g of isolated mitochondria alone or mitochondria plus 4 μg of the transcribed RNA. A rabbit reticulocyte lysate kit was used following the instructions of the manufacturer (Du Pont-NEN, Boston, Mass.). The proteins were synthesized in the presence of [$^{35}$S]-methionine for 1 h at 37° C. and the reactions were frozen at −20° C. An equal volume of each reaction was analyzed by two-dimensional SDS-PAGE as described above. The gels were prepared for fluorography using Resolution (E.M. Corp., Chestnut Hill, Mass.), dried under moderate heat and vacuum, and exposed to x-ray film at −80° C.

Expression of the 30-kD Protein in MA-10 Cells and COS I Cells. The full length SalI-NotI 1456 base pair 30-kDa cDNA was subcloned into the eukaryotic expression vector, pCMV (Anderson, et al., 1989). MA-10 cells were transfected with DNA by a lipsome-mediated uptake using the LipofectAMINE reagent (Life Technologies, Inc. Gathersburg, Md.) (Hawley-Nelson, et al., 1993). Plasmid DNA used in transfection experiments were purified by CsCl density gradient followed by polyethylene glycol precipitation. The DNA was mixed with 1/10 the final volume of Waymouth's media minus serum and minus antibiotics ($WAY^-$) and added to an equal volume of $WAY^-$ media containing the LipofectAMINE reagent. The DNA/lipid solution was gently mixed and incubated for 30 min at room temperature, then $WAY^-$ media was added to achieve the final concentration of the DNA and LipofectAMINE reagent of 5 μg/ml and 20 μg/ml respectively. The cells were washed once with $WAY^-$ media, incubated with transfection mix for 6 h, washed once with PBS, then incubated with Waymouth's plus 15% horse serum. The same procedure was used for transfection of COS 1 cells except Dulbecco's modified Eagle's media minus serum and antibiotics was used for the transfection media. For isolation of mitochondria for immunoblot analysis, cells were grown on 100-mm dishes. For progesterone production assays, MA-10 cells were plated into 96 well plates at 75,000 cells/well the day before the experiment. Typically, 8 wells each were transfected with either pCMV or pCMV+30-kDa cDNA for one experiment set.

A reporter construct expressing a tartrate-resistant acid phosphatase (TRAP) was used to determine the efficiency of transfection of MA-10 cells by the LipofectAMINE reagent. The tatrate-resistant acid phosphatase expression plasmid contains the full-length human cDNA cloned into the pcDNA1 vector provided by Dr. G. D. Roodman (Univ. of Texas HSC, San Antonio, Tex.) (Reddy, et al., 1993). Forty-eight hours post-transfection the cells were fixed directly in the wells with 2% glutaraldehyde, then stained for tartrate-resistant acid phosphatase activity using an acid phosphatase staining kit (Sigma Chemical Co., St. Louis, Mo.). Several wells of MA-10 cells were transfected with the tartrate-resistant acid phosphatase expression plasmid for each experiment and the positively stain cells were counted visual inspection using an inverted light microscope. Typically, 5–7% of the cells were stained positive for tartrate-resistant acid phosphatase expression.

Immunoblot Analysis. Mitochondria were isolated from either MA-10 or COS 1 cells transfected with either pCMV or pCMV+30 kDa cDNA 48 hours post-transfection. For experiments in which progesterone production was measured (as described above), cells were solubilized directly in the well with 0.1% SDS, the cell homogenates were collected and combined from all 8 wells, and the protein was precipitated using trichloracetic acid. The protein was solubilized in sample buffer (25 mM Tris/Cl, pH 6.8, 1% SDS, 5% β-mercaptoethanol, 1 mM EDTA, 4% glycerol, and 0.01% bromophenol blue) and loaded onto a 12.5% SDS-PAGE minigel (Mini-Protein II System, Bio-Rad, Richmond, Calif.). Electrophoresis was performed at 200 V for 45 min using standard SDS-PAGE buffer as described above, and the proteins were electrophoretically transferred to a polyvinylidene difluoride membrane (Bio-Rad) at 100 V for 2 h at 4° C. using the transfer buffer described above. For immunodetection of the 30 kDa protein, antipeptide antibodies were generated in rabbits against amino acids 88-98 of the 30 kDa proteins (FIG. 2). The peptide was synthesized and the antibodies were produced in rabbits on a fee for service basis by Research Genetics (Huntsville, Ala.). The immunoblot procedure was as follows; the membrane was incubated in blocking buffer (PBS buffer containing 4% Carnation non-fat dry milk and 0.5% Tween-20) at room temperature for 1 h, then incubated in fresh blocking buffer containing the primary label (rabbit sera containing the specific antipeptide antibodies) for an additional hour at room temperature. Next, the membrane was washed PBS containing 0.5% Tween-20, 3 times for 10 min each wash, then incubated for 1 h at room temperature with fresh blocking buffer containing the secondary antibody, donkey anti-rabbit IgG conjugated with horseradish peroxidase (Amersham Life Sciences, Arlington Heights, Ill.). The membrane was washed as before, and the specific signal was detected by chemiluminescence using the Renaissance kit from Du Pont-NEN.

Polyclonal antiserum has been generated to presequences of StAR, in particular, to a signal sequence from amino acid 10 to 26 of SEQ ID NO:2, and to a targeting sequence from amino acid 36 to 47 of SEQ ID NO:2. Antibodies of these polyclonal antisera were tested and immunoreact with precursor forms of StAR. Further polyclonal antiserum was generated to signal sequence from amino acid 1 to 26 of SEQ ID NO:2, this antiserum reacts with the signal peptide.

Radioimmunoassay. 48 hours post-transfection, the growth medium was replaced with Waymouth's minus horse serum. After 6 h at 37° C. 5% $CO_2$, progesterone was measured directly in the media by radioimmunoassay as previously described (Resko, et al., 1974). The progesterone antibody was obtained from Holly Hill Biologicals (Hillsboro, Oreg.).

The following examples are included to demonstrate preferred embodiments of the invention. It should be appreciated by those of sill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Purification of 30-kDa Proteins 1 and 2

The present example provides for the purification of the 30 kDa proteins 1 and 2. The family of LH-inducible proteins previously identified and characterized by the present inventors in mitochondria isolated from MA-10 cells represented approximately 0.2% of the total cell protein and 0.7% of the mitochondrial protein (Table 3). Due to the limited amount of the in vivo induced protein, the present inventors purified the 30 kDa proteins from the mitochondria by enriching a postmitochondrial fraction for the specific 30 kDa proteins and separating the enriched fraction by two-dimensional SDS-PAGE. The proteins were electrophoretically transferred to nitrocellulose, and the specific 30 kDa proteins were isolated by excising the nitrocellulose spot containing the bound protein. The purification scheme developed to isolate the 30 kDa proteins is summarized under "Materials and Methods" hereinabove. The objective was to isolate a sufficient amount of the 30 kDa protein for in situ tryptic digestion, peptide separation, and microsequence analysis.

Proteolytic digestion of each of the 30 kDa forms produced identical peptides, indicating that the difference in these four forms is due to post-translational modifications of a single proteins. The present inventors had previously shown that the difference in the isoelectric points for forms 3 and 4 is due to phosphorylation of forms 1 and 2. The 30 kDa mitochondrial proteins are processed from a larger precursor protein synthesized in response to hormone stimulation of MA-10 cells. However, the precursor protein has a short half-life and is difficult to detect in MA-10 cells (Stocco and Sodeman, 1991; Epstein and Orme-Johnson, 1991). For this reason the present inventors focused on the purification of the 30 kDa proteins which are stable in mitochondria isolated from MA-10 cells. These proteins had been detected by metabolically labeling MA-10 cells in vivo with [$^{35}$S]-methionine/cysteine and isolating the mitochondria for two dimensional SDS-PAGE analysis followed by fluorography.

The present inventors first determined if the quantity of the 30 kDa proteins in isolated mitochondria was sufficient to detect by protein staining. The 30 kDa proteins were readily detectable by silver-stain after two dimensional SDS PAGE of mitochondria isolated from $Bt_2$cAMP-stimulated MA-10 cells. As expected, the proteins were absent in unstimulated cells. The major difficulty in the purification of the 30 kDa proteins MA-10 cells were the lack of a bioassay, therefore each step of the purification was monitored by silver-stained two dimensional SDS PAGE analysis of the proteins.

Table 3 summarizes the enrichment and recovery of the 30 kDa proteins.

TABLE 3

Purification of the 30-kDa Proteins from $Bt_2$cAMP-stimulated MA-10 Cells[1]

| Fraction | Total protein % recovery | μg 30-kDa proteins/ mg sample protein | Enrichment of the 30-kDa proteins -fold enrichment | % recovery 30-kDa proteins |
|---|---|---|---|---|
| Mitochondria | 100 | 7 | 1 | 100 |
| Mitoplasts | 56 ± 10 | ND[a] | ND | ND |
| CHAPS-soluble | 22 ± 6 | 18 | 2.6 | 55 |
| 30-kDa fraction | 0.6 ± 0.3 | 94±28 | 13 | 7 |

n = 16

1 Shown are the results from the purification of the 30-kDa proteins from 40–50 mg of mitochondria. Each fraction was separated by two dimensional-gel electrophoresis and the proteins were visualized by silver stain. 1 gel was analyzed for the mitochondrial fraction, 2 gels with different protein concentrations for the CHAPS-soluble fraction, and 4 gels with varying protein concentrations for the 30-kDa fraction were run simultaneously and stained for protein. The silver-stained image was captured, and the integrated intensity (II) of each spot (protein) was estimated using a BioImage Visage 2000 (Millipore). The percent of the total integrated intensity of each spot/protein was automatically determined. To estimate the amount of 30-kDa protein, the percent of total II for the 30 kDa protein spots were multiplied by the amount of total protein loaded onto the first dimension gel. The results are shown as micrograms 30-kDa protein (sum of 1–4) per mg of fraction sample.

[a]ND, mitoplast fraction not determined.

The purification achieved a 13-fold enrichment with a 7% recovery of the 30 kDa proteins. The goal was to sufficiently enrich the 30 kDa proteins in a final fraction in order to resolve a sufficient quantity (1–2 μg) of the specific 30 kDa proteins by 2D SDS-Page. The 1D preparative gel enriched the 30 kDa proteins to approximately 100 μg/mg of the final 30 kDa fraction which allowed the present inventors to isolate the 30 kDa protein. The 30 kDa fraction was treated with alkaline phosphatase just prior to 2D SDS-PAGE to concentrate to 30 kDa proteins into forms 1 and 2 (Stocco and Clark, 1993). Comparison of the protein profiles for the 30 kDa fraction purified from mitochondria isolated from control and $Bt_2$cAMP-stimulated MA-10 cells was used to verify that the correct protein spots, 30 kDa 1 and 2, were isolated. Using this purification, approximately 75 mg of isolated mitochondria was required to isolate approximately 200 pmol of the 30 kDa proteins from $Bt_2$cAMP-stimulated MA-10 cells. Quantitatively, 60% of the total 30 kDa proteins was recovered in 30 kDa 2, and 40% was recovered in 30 kDa 1. The difference between form 1 and form 2 maybe that of methylation, acetylation, sulfation, prenylation, or myristylation, and the like.

EXAMPLE 2

Cloning the cDNA and Analysis of the Encoded 30 kDa Protein

The present example provides for the cloning and sequence analysis of the cDNA encoding the 30 kDa protein, and analysis of the protein sequence. Even though 30 kDa 1 and 30 kDa 2 were thought to be identical proteins, they were isolated and stored separately. To ensure one homogeneous protein was used for microsequence analysis, only the 30 kDa protein 2 was sent to the Harvard Microchemical Facility where in situ digestion, tryptic peptide separation, and microsequence analysis was performed on a fee-for-service basis. Three tryptic peptides, #23, #25, and #45, were selected for microsequence analysis. The amino acid sequences for the peptides were determined to be:

Peptide 23: AEHGPTCMVLHPLA, (SEQ ID NO:3)

Peptide 25: ALGILNNQEGWK, (SEQ ID NO:4)

Peptide 45: GSTCVLAGMATHFGEMPEQ, (SEQ ID NO:5)

The GenEMBL and SWISS-PROT data bases were searched for similarities to the three peptides sequences and no significant homologies were found (Fasta and TFasta programs, GCG Package, University of Wisconsin, Madison, Wis.).

A cDNA library was constructed using polyA$^+$ RNA purified from total RNA that was isolated from $Bt_2$cAMP-stimulated MA-10 cells as described hereinabove. Using the amino acid sequence of the 3 peptides, degenerative oligonucleotides 17–24 bases in length were synthesized and used to amplify the 30 kDa cDNA from the cDNA library by the polymerase chain reaction (PCR)(Saiki et al., 1988). A 400 bp specific PCR product was amplified using a combination of the peptide 25 coding and peptide 23 reverse complement oligonucleotides. The PCR generated DNA was used to probe the cDNA library and a 1456 bp full-length clone was isolated. Both strands of the cDNA were sequenced and a partial restriction map is shown in FIG. 1. Also included are the positions of the PCR amplified sequence, the initiating ATG codon, and the termination TAA codon. FIG. 2 shows the nucleotide sequence of the 30 kDa cDNA which contains an open reading frame of 852 base pairs that encodes a protein of 284 amino acids with a calculated molecular weight of 31.6 kDa. The deduced amino acid sequence for the 30 kDa protein is shown by three letter code under the nucleic acid sequence. The three peptide sequences derived from the protein microsequence analysis are encoded in the cDNA (the amino acids are underlined in FIG. 2) which confirmed the translation reading frame.

Although the predicted molecular weight based on the deduced amino acid sequence is lower than the observed size of the mitochondrial precursor protein by 2D SDS-PAGE, inspection of the amino terminal amino acid sequence for the deduced protein revealed characteristics consistent with mitochondrial targeting sequences (von Heijne, 1986; von Heijne et al., 1989). Namely, the first 25 amino acids lack acidic amino acids, are enriched in Arg (12%), Ser (8%), Ala (8%), and Leu (12%), and the predicted secondary structure is an amphipathic alpha helix. In addition, the amino acids at positions 38, 409, and 43 are Arg, Leu, and Ser, respectively, which would fit the amino acid consensus cleavage site, R-X-Φ-X-X-S, where X represents any amino acid Φ represents a hydrophobic residue (Hendrick, et al., 1989). This amino acid motif is highly conserved in mitochondrial presequences that undergo a 2 step sequential cleavage of mitochondrial precursors by the matrix processing protease (MPP) and the mitochondrial intermediate processing peptide (MIP) (Kalousek, et al., 1988; Kiebler et al., 1993). No significant similarities were found to the cDNA sequence when the GenEMBL and SWISS-PROT data bases were searched.

The signal sequence is represented by amino acids at positions 1 to about 26 of SEQ ID NO:2, more particularly, from about amino acids at positions 10 to 26 of SEQ ID NO:2. The targeting sequence is represented by amino acids at about positions 36 to 47 of SEQ ID NO:2. The mature 30 kDa protein has methionine at position 48 as the N-terminal amino acid.

To confirm that the cDNA clone encodes the precursor and mature mitochondrial proteins, the cDNA was transcribed in vitro and the synthesized RNA was used in an in vitro translation reaction. A two dimensional SDS-PAGE of the [$^{35}$S]-methionine labeled in vitro translated proteins in the presence of mitochondria demonstrated that the mobility of the proteins was identical to the LH-induced newly synthesized proteins in MA-10 cells which were previously identified as the 37 kDa precursor protein and the 30 kDa mitochondrial proteins. Therefore, the cDNA obtained based on the amino acid sequence data for the 30 kDa 2 protein encodes all forms of the previously described family of mitochondrial proteins.

EXAMPLE 3

Improved Production of Progesterone and StAR protein by Recombinant Means; Induction of Steroidogenesis The present example demonstrates that the expression of the 37 kDa protein has an effect on steroid production in mammalian cells.

MA-10 cells were transfected with the 30 kDa cDNA and progesterone production was measured as follows. The full-length cDNA was subcloned into the pCMW eukaryotic expression vector and transfected into MA-10 cells using LipofectAMINE (Life Technologies, Inc.). Cells (75,000 per well) were plated in a 96 well plate the day before transfection. The cells were incubated with the DNA/lipid transfection mixture for 6 hours, washed one time with PBS, and the incubated in Waymouths+15% horse serum. Forty-eight hours post-transfection the cells were washed with PBS and Waymouths media (minus serum) was placed back onto the cells. After 6 h, the medium was removed and progesterone was measured by radioimmunoassay. The cells were lysed directly in the wells with 0.1% SDS and protein was determined by the method of Bradford (1976). Progesterone production is shown in Table 4 as picograms progesterone produced per mg protein per 6 h. The transfected cells were not treated with hormone and progesterone was measured directly in the media after a 6 h incubation. A significant increase in progesterone production was observed in MA-10 cells transfected with the 30 kDa cDNA compared to cells transfected with the pCMV vector alone (Table 4). Expression of the 30 kDa protein resulted in a 1.5 to 3.7 fold increase in steroidogenesis with an average rate of 166 pg progesterone produced per mg protein per hour.

TABLE 4

Progesterone production in MA-10 cells transiently transfected with the 30 kDa cDNA[1]

| Study[2] | n | Control (nontrans-fected) | pCMV pg progesterone/mg protein/6 h | pCMV + cDNA | pCMV + cDNA/pCMV -fold increase[2] |
|---|---|---|---|---|---|
| I | 3 | ND[3] | 361 ± 38 | 1239 ± 347 | 3.4 |
| II | 4 | ND | 317 ± 77 | 519 ± 42 | 1.6 |
| III | 8 | ND | 403 ± 145 | 1775 ± 444 | 3.7 |
| IV | 8 | 756 ± 135 | 787 ± 174 | 1148 ± 174 | 1.5 |
| V | 8 | 469 ± 58 | 428 ± 81 | 1378 ± 233 | 3.2 |
| VI | 8 | 779 ± 171 | 1071 ± 143 | 3146 ± 768 | 2.9 |

[1]Control (non-tansfected) cells were grown in WAY + for 48 h and washed once with PBS + before WAY − media was added; pCMV, MA-10 cells were transfected with the pCMV vector alone; pCMV + cDNA, MA − 10 cells were transfected with the pCMV + 30 kDa cDNA.
n represents the number of wells transfected for each experiment. The progesterone was measured in each well and the mean ± the standard deviation is shown for each study. The Student's t test was used to determine the statistical difference between the pCMV and pCMV + 30 kDa cDNA samples.
[2]In every study, the difference was significant with a p value < 0.01.
[3]ND, not determined.

The level of expression of the 30 kDa protein in the transfected MA-10 cells was determined by immunoblot analysis. Antibodies having binding specificity for amino acid 88–98 of the 30 kDa proteins (see Materials and Methods) recognized a protein at approximately 30 kDa only in mitochondria isolated from $Bt_2$cAMP-stimulated MA-10 cells while no immunodetectable protein was observed in the non-stimulated cells. In addition, the antibody recognized all four 30-kDa protein spots specifically when mitochondrial proteins from stimulated MA-10 cells were resolved by two-dimensional SDS-PAGE. Cell homogenates of the MA-10 cells that had been transfected with pCMW+30 kDa cDNA and used for progesterone production for expression of the 30 kDa protein were tested, however, no immunodetectable protein was observed. Since the pCMV vector does not replicate in MA-10 cells, and only 5% of the cells are transfected with plasmid DNA based upon expression of the tartrate-resistant acid reporter protein, it was not surprising that the protein could not be detected in cell homogenates collected from approximately $1\times10^6$ cells (8 wells from a 96 well plate).

In order to verify that the cDNA was being expressed in eukaryotic cells, COS 1 cells were used to transfect the pCMV+30 kDa cDNA since the pCMV plasmid can be replicated in these cells and approximately 80% of the cells are transfected with plasmid DNA based on the expression of reporter protein. Forty-eight hours post-transfection, mitochondria were isolated and the 30 kDa protein expression was determined by immunoblot analysis. An immunospecific protein of approximately 30 kDa was readily detectable in isolated mitochondria only from COS I-cells that had been transfected with the 30 kDa cDNA, indicating the cDNA does express the same protein as the $Bt_2$cAMP-stimulated MA-10 cells. In addition, a 36.5 kDa protein was detected in the COS 1 cells which would be consistent with the precursor protein. Importantly, the 30 kDa protein was also detectable in MA-10 cells transfected with pCMV+30 kDa cDNA by immunoblot analysis when isolated mitochondria were analyzed. The level of expression of the 30 kDa protein in the transfected MA-10 cells was approximately 7% of that observed in the $Bt_2$cAMP-stimulated MA-10 cells. Thus, these data indicate that the expression of the 30 kDA protein is sufficient to induce steroid production in MA-10 cells in the absence of hormone stimulation.

The present inventors have named this protein the Ŝteroidogenic Âcute R̂egulatory protein, StAR. While not wishing to be bound by any particular theory regarding a mechanism of action, the following working model for the acute regulation of steroidogenesis in Leydig cells by StAR is provided. The precursor protein is rapidly synthesized in the cytosol in response to hormone stimulation. The precursor binds to a receptor on the mitochondrial membrane and processing begins. Processing consists of the N-terminus entering the mitochondrial matrix and being cleaved to the 30 kDa form. It is during the processing that contact sites between the inner and outer mitochondrial membranes form and this very hydrophobic environment provides the medium through which cholesterol may pass to the inner membrane. Thus, it may be the processing of StAR from a 37 kDa form to a 30 kDa form that is functionally active in the transport of cholesterol and results in increased steroid production. This protein is also demonstrated to bind cholesterol (See Example 18).

EXAMPLE 4

Expression of StAR Precursor Protein in *E. coli*

The present example describes studies carried out to express the 37 kDa precursor StAR protein in *E. coli* for overproduction thereof.

The *E. coli* expression vector, pKK233-2, (Clontech, Palo Alto, Calif.) contains an IPTG-inducible promoter ($P_{trc}$), a LacZ ribosome binding site, and a unique NcoI cloning site that provides an ATG initiation codon. Since expression of mitochondrial proteins tends to be toxic to bacterial host cells, basal levels of expression can be greatly reduced *E. coli* strains that overproduce the lac repressor ($lacI^q$) and optimal expression can be achieved by induction for a short period of time.

StAR cDNA was cloned in pSPORT vector (GIBCO *Life Technologies,* Gaithersburg, Md.) and this vector was used for PCR amplification of the coding sequence for StAR. Primers were designed to introduce restriction sites (NcoI at the 5' end and HindIII at the 3' end) for directional subcloning into the pKK233-2 vector. Ligation of the amplified StAR cDNA fragments with the pKK233-2 vector constructed a recombinant pKK233-2/StAR plasmid. The *E. coli* strains, JM109 and DH5αF'IQ, were transformed with this plasmid and maintained in LB media (10 g tryptone, 5 g yeast extract, 10 g NaCl, and 100 μg/ml ampicillin). For expression, a fresh culture (15–30 ml LB media) inoculated with the transformed *E. coli* was grown to an $OD_{600}$=0.6 at 37° C. then IPTG (isopropyl β-D-thiogalactopyranoside) was added to a final concentration of 1 mM. Protein expression was induced at 30° C. for 2 hours and cells were harvested. Cells were lysed by sonication in buffer containing 50 mM Tris (pH 8.0), 150 mM NaCl, 0.02% sodium azide, 0.1% SDS, 1% NP-40, 0.5% sodium deoxycholate, 100 μg/ml phenylmethylsufonyl fluoride, 2 μg/ml aprotinin, and 2 μg/ml leupeptin.

From staining patterns on gels, it is apparent that significant amounts of StAR protein were made. The extract of *E. coli* DH5αFIQ with the StAR cDNA insert contained a 37 kDa polypeptide which was approximately 3% of the total cellular protein. This 37 kDa protein was not detected in *E. coli* without the plasmid. The protein reacted with the antibody raised against amino acids 88–89 of StAR.

For isolation and purification of the StAR precursor protein, the sonic lysate was ultracentrifuged (100,000 x g, 1H), and the supernatant passed through an affinity column packed with Protein A agarose beads crosslinked with the anti-StAR antibody having binding specificity for amino acids 88–98 of StAR. The fractions enriched for StAR precursor protein were concentrated and further purified by passage through a gel filtration column (packed with Sephadex G-75 beads). Flow-through fractions were tested for the StAR precursor protein by Western blot analysis and the purity was assayed using a silver staining method.

EXAMPLE 5

StAR is Hormonally Regulated and Developmentally Regulated

The present example provides studies that show that the production of StAR protein is hormonally regulated, as well as developmentally regulated in vivo.

MA-10 cells were stimulated with $Bt_2$cAMP and StAR mRNA levels were determined by Northern blot analysis. Within 1 hour of $Bt_2$cAMP stimulation, two major transcripts of approximately 3400 nt and 1600 nt, and one minor transcript of 2700 nt, were detected. StAR mRNAs were markedly induced (20x) after 2 hours of hormone stimulation with maximal levels obtained after 6 hours. Subsequent to the marked mRNA induction, the greatest induction (10x) in StAR protein was detected after 4 hours of $Bt_2$cAMP stimulation by immunoblot analysis. Comparatively lower levels of StAR could be detected after 1 hour of hormone stimulation with maximal levels accumulated within 8 hours.

Hormone-induced progesterone production rose above basal levels in MA-10 cells typically within 1 hour with the greatest increase in rate of steroid output measured between 2–4 hours of hormone stimulation, consistent with the induction in StAR protein.

These data indicate that StAR is transcriptionally regulated by a cAMP-mediated mechanism. Immunoblot analysis of several mouse tissues indicates that StAR protein is expressed in the adrenal, ovary, and testis, and is not expressed in brain, muscle, liver, kidney, spleen, heart, uterus, or placenta. The developmental expression of StAR was assessed by in situ hybridization analysis of mouse embryonic tissue. Earliest detection of StAR transcripts was at embryonic day 10.5 (E10.5) in the genital ridge. By E12.5–E14.5, StAR was readily detected in the interstitial cells of the testis and adrenal cortex and continued to be expressed in the adult. StAR expression was absent in the ovary at E12.5–E14.5, but was abundant in the adult ovary. The developmental pattern of expression for StAR parallels that observed previously for cytochrome P450scc which provides further supporting evidence for the importance of StAR in steroid hormone biosynthesis.

The present inventors have generated stable transfected MA-10 cell lines that constitutively synthesize the 30 kDa protein and that produce steroid constitutively at a level several fold higher (about 9x) than basal parental MA-10 cells.

EXAMPLE 6

Screening for Mutations in the StAR Gene for Identifying Steroid Hormone-Dependent Pathologies The present example provides methods by which the nucleic acid molecules, in particular, fragments of the nucleotide sequence of SEQ ID NO:1 or SEQ ID NO:15 may be used to detect mutations within the StAR gene. These screening techniques may be used to identify a number of different pathologies; particularly steroid hormone-dependent pathologies, such as, for example, lipoid congenital adrenal hyperplasia (LCAH), adrenal hypoplasia congenita, hypogonadotropic hypogonadism, precocious puberty, or McCune-Albright syndrome.

The identification of highly conserved mutations and the development of an appropriate screen would provide regulations and standards for clinical testing and screening for these metabolic disorders.

Lipoid Congenital Adrenal Hyperplasia (LCAH)

StAR DNA may be used for screening adrenal tissue obtained from patients with Lipoid Congenital Adrenal Hyperplasia (LCAH) to test for a possible role of StAR in the disease state. This can be achieved with Southern blotting and hybridization with a cDNA probe. Fairly large DNA rearrangements of greater than 500 by may be detected in this manner. However, it may be that the mutations within the StAR gene resulting in steroid hormone-dependent pathologies are too small to detect by Southern blotting. This would be the case if they are due to point mutations or to small insertions, deletions or other rearrangements.

Smaller StAR gene mutations are detected by DNA sequencing which can be performed on a genomic DNA template, a cDNA template prepared from RNA by reverse transcriptase, or on a PCR product. In an attempt to detect mutations rapidly, several methods are available; chemical cleavage, denaturing gradient electrophoresis (DGGE) and ribonuclease cleavage, and single strand conformation polymorphism. These methods and others may be used in conjunction with the present invention and may be performed after PCR amplification of the DNA region under study.

Testicular tissue of two patients and genome DNA of a third patient with LCAH have mutations in the gene for StAR (Lin et al., Science, 267:1828–1831, 1995) (incorporated herein by reference). These mutations consist of C to T transitions in the gene sequences, which resulted in the premature insertion of stop codons. This resulted in the truncation of StAR protein by 28 amino acids in two of the patients and 93 amino acids in another. These truncations were confirmed by Western analysis following expression of the mutated cDNAs in COS cells. Virtually none of the precursor form of StAR expressed from the cDNA of these patients was converted to the mature mitochondrial form. Expression of the StAR cDNA from these patients in COS1 cells indicated that the protein produced was inactive in its ability to promote steroidogenesis, whereas the normal protein resulted in an 8-fold increase in steroid production when expressed.

EXAMPLE 7

Gene Therapy

This prophetic example describes some of the ways in which the present invention may be of use in the treatment of steroid hormone-dependent disorders, especially those characterized as involving defects in cholesterol transport.

A wild-type human StAR gene may be introduced into human tissue to provide a wild-type copy of the gene and therefore, also a wild-type protein product, that may correct the genetic lesion that causes the steroid hormone-dependent disorder.

Human adenovirus or retrovirus are means for introducing genes into tissue. Adenoviruses are double-stranded DNA tumor viruses with genome sizes of approximate 36 kb. As a model system for eukaryotic gene expression, adenoviruses have been widely studied and well characterized, and have already been used in a gene transfer system (see e.g., WO9506743, WO9502697, WO9500655, WO9428938, WO9419478, and WO9412649, each publication is incorporated by reference herein). This group of viruses is easy to grow and manipulate, and they exhibit a broad host range in vitro and in vivo. In lytically infected cells, adenoviruses are capable of shutting off host protein synthesis, directing cellular machineries to synthesize large quantities of viral proteins, and producing copious amounts of virus.

In general, adenovirus gene transfer systems are based upon recombinant, engineered adenovirus which is rendered replication-incompetent by deletion of a portion of its genome, such as E1, and yet still retains its competency for infection. Relatively large foreign proteins can be expressed when additional deletions are made in the adenovirus genome. For example, adenoviruses deleted in both E1 and E3 regions are capable of carrying up to 10 Kb of foreign DNA and can be grown to high titers. Persistent expression of transgenes follows adenoviral infection.

Particular advantages of an adenovirus system for delivering foreign genes and their protein products to a cell include (i) the ability to substitute relatively large pieces of viral DNA with foreign DNA; (ii) the structural stability of recombinant adenoviruses; (iii) the safety of adenoviral administration to humans; and (iv) lack of any known association of adenoviral infection with cancer or malignancies; (v) the ability to obtain high titers of the recombinant virus; and (vi) the high infectivity of adenovirus.

Further advantages of adenovirus vectors over retroviruses include the higher levels of gene expression. Additionally, adenovirus replication is independent of host gene replication, unlike retroviral sequences. Because adenovirus transforming genes in the E1 region can be readily deleted and still provide efficient expression vectors, oncogenic risk from adenovirus vectors is thought to be negligible.

Patients testing positive for LCAH and for whom the medical indication for adenovirus-mediated gene transfer has been established, would be tested for the presence of antibodies directed against adenovirus. If antibodies are present and the patient has a history of allergy to either pharmacological or naturally occurring substances, application of a test dose of on the order of $10^3$ to $10^6$ recombinant adenovirus under close clinical observation would be indicated.

Recombinant adenovirus providing the wild-type StAR gene may be prepared and purified by any of a variety of methods, so as to provide a preparation suitable for administration to human subjects, including, but not limited to cesium chloride density gradient centrifugation, and subsequently tested for efficacy and purity. Virus is administered to patients by means of intravenous administration in any pharmacologically acceptable solution, either as a bolus or as an infusion over a period of time. Generally speaking, it is believed that the effective number of functional virus particles to be administered would range from $5\times10^{10}$ to $5\times10^{12}$.

Patients would remain hospitalized for at least 48 hr to monitor acute and delayed adverse reactions. Serum levels of a protein product may be monitored or Southern blots may be performed to follow the efficacy of the gene transfer. Adjustments to the treatment may include adenovirus constructs that use different promoters or a change in the number of pfu injected.

EXAMPLE 8

Expression of StAR induces Steroid Production in the absence of Hormone Stimulation The present example demonstrates that StAR expression induces steroid production in the absence of hormone stimulation.

Transient transfection of COS 1 cells with StAR resulted in a several fold increase in steroid production in the absence of hormone stimulation. Transient transfection of COS 1 cells with StAR was observed to provide in a several fold increase in steroid production. Also, increases in StAR mRNA and protein closely paralleled steroid production indicating a temporal relationship in these parameters.

EXAMPLE 9

Calcium Stimulates StAR Protein

The effect of changes in $[Ca^{2+}]_c$ on intramitochondrial cholesterol and the distribution of StAR protein in mitochondria during activation by $Ca^{2+}$ is described in the present example.

In adrenal glomerulosa cells, angiotensin II (Ang II) stimulates aldosterone synthesis through rises of cytosolic calcium, $[Ca^{2+}]_c$. The rate-limiting step is the transfer of cholesterol to the inner mitochondrial membrane, where it is converted to pregnenolone by the P450 side chain cleavage enzyme ($P450_{scc}$). This transfer is believed to occur as the 37 kDa precursor of the Steroidogenic Acute Regulatory (StAR) protein is imported into the mitochondria.

Freshly-prepared bovine zona glomerulosa cells were stimulated with Ang II (10 nM) or submitted to a cytosolic $Ca^{2+}$ clamp (600 nM) for 2 h. Mitochondria were isolated and subfractionated into outer membranes (OM), inner membranes (IM) and contact sites (CS). Cholesterol content was determined by the cholesterol oxidase assay.

When glomerulosa cells were exposed to Ang II, a marked increase of cholesterol in CS occurred (to 172±28% of controls, n=3). No significant changes were detected in OM cholesterol, suggesting a stimulation of cholesterol supply to the mitochondria in response to Ang II. Stimulation of intact cells with $Ca^{2+}$ lead to a marked decrease in cholesterol content of OM (to 54±24% of controls, n=5). Cycloheximide specifically and significantly reduced $Ca^{2+}$ -activated cholesterol transfer to IM. Western blot analysis revealed a cycloheximide-sensitive increase of StAR protein (to 141±14% of controls, n=5) in mitochondrial extracts of $Ca^{2+}$-mobilizing agents, newly synthesized StAR accumulates in IM after transiting through CS. One of the main functions of the $Ca^{2+}$ messenger is to increase cholesterol supply to the $P450_{scc}$ enzyme by enhancing endogenous intermembrane cholesterol transfer. The import of StAR protein to IM is accompanied by cholesterol transfer, thus promoting the activation of the steroidogenic cascade.

EXAMPLE 10

Angiotensin II Stimulates Intramitochondrial Cholesterol Transfer and StAR Protein in Bovine Adrenal Glomerulosa Cells The effect of Ang II on intramitochondrial cholesterol and the distribution of StAR protein in submitochondrial fractions during activation by Ang II is described in the present example.

Freshly-prepared bovine zona gomerulosa cells were stimulated with Ang II (10 nM) or submitted to a cytosolic $Ca^{2+}$ clamp (600 nM) for 2 h, as described in Example 9. Mitochondria were isolated and subfractionated into outer membranes (OM), inner membranes (IM) and contact sites (CS). Cholesterol content was determined by the cholesterol oxidase assay, also as described in Example 9.

StAR protein in Ang II stimulated (to 157% of controls, n=2) glomerulosa cells. Ang II increased StAR in IM, and this effect was prevented by cycloheximide.

EXAMPLE 11

StAR and a Water Soluble CaM Kinase II Inhibitor

The present example demonstrates the effect of a water soluble CaM kinase II inhibitor on the agonist inductor of StAR protein. The water soluble CaM kinase inhibitor, KN93, was used in the present example and is representative of the water soluble CaM kinase II inhibitors generally.

The human adrenocortical carcinoma-derived cell line (H295R) was used. This cell line secretes multiple steroids, including aldosterone and cortisol. This cell line is an appropriate model system to investigate the acute regulation of human aldosterone synthesis, as described in Bird et al (1993) (Endocrinology, 133, 1555–1561), which is specifically incorporated herein by reference.

To further investigate the site of KN93 action, the effect of KN93 on agonists induction of the StAR protein, shown herein to regulate movement of cholesterol from the outer to the inner mitochondrial membranes, was examined. The amount of StAR protein was increased following treatment of H295R cells with angiotensin II (Ang II) potassium (K), and Bay K (a calcium channel activator) as shown by the present investigation (See Clark et al., 1995, Mol. Cell Endocrinol., 155:215–19). KN93 at concentration between 1 and 3 μM, which blocked steroidogenesis by 60 to 80%, did not affect induction of StAR protein by Ang II, $K^+$, or Bay K. These results support the finding that CaM kinase II is involved in the process of cholesterol mobilization to the mitochondria.

Materials and Methods

Materials

[$Val^5$]-Angiotensin II acetate (Ang II), potassium chloride, 22R-hydroxylcholesterol (22ROHChol), d-aldosterone, hydrocortisone (cortisol) and laboratory reagents were from Sigma Chemicals (St. Louis, Mo.). Dibutyryl cAMP (dbcAMP) was from Aldrich Chemicals (Milwaukee, Wis.) (=)-Bay K 8644 (Bay K) was from Research Biochemicals International (Natick, Mass.). The protein kinase inhibitor KN93 (2-[N-(2-hydroxyethyl)-N-(4-methoxybenzenesulfonyl)]amino-N-(4-chlorocinnamyl)-N-methylbenzylamine) was from Seikagaku America, Inc. (Ijamsville, Md.). The calmodulin inhibitor compounds R 24571 (calmidazolium) was from Janssen Pharmaceutica (Berse, Belgium).

Cell culture

H295R cells were initially obtained as NCI-H295 cells from the American Type Culture Collection (Rockville, Md.), and then selected as described previously (Bud et al. (1993)). Reflecting growth and culture differences between the original ATCC cells and the selected subpopulation, these cells are designated as H295R cells and are available from ATCC as such. Cells were maintained in a 1:1 mixture of Dulbecco's modified Eagle's and Ham's F12 (DME/F12) medium containing pyridoxine HCl, L-glutamine and 15 mM Hepes (Gibco BRL; Gaithersberg, Md.); medium was supplemented with insulin (6.25 μg/ml), transferrin (6.25 μg/ml), selenium (6.25 ng/ml), bovine serum albumin (1.25 mg/ml), and linoleic acid (5.35 μg/ml) added in the form of 1% ITS plus (Collaborative Biomedical Products; Bedford, Mass.). In addition, cells were grown in the presence of either 2% low protein serum replacement (Sigma Chemicals; St. Louis, Mo.) or 2.5% Nu serum type I (Collaborative Biomedical Products; Bedford, Mass.) as well as antibiotics. Cells were maintained and grown in 75 $cm^2$ flasks at 37° C. under an atmosphere of 5% $CO_2$/95% air, subcultured onto 12 well plates and used for experiments 48 hours later as indicated below.

Stimulation of steroid secretion and analysis of steroids

Subcultured cells were maintained 24 hours in DME/F12 medium containing 0.2% calf serum, 0.01% BSA and antibiotics (low serum). Cells were preincubated with KN93 or calmidazolium for 30 minutes at 37° C. Fresh low serum medium containing the agents as indicated was then added to the cells and the incubation carried out at 37° C. for the indicated times. The aldosterone and cortisol contents of medium recovered from each well were determined with aldosterone and cortisol standards prepared in low-serum medium by commercial aldosterone and cortisol radioimmunoassays (Diagnostic System Laboratories; Webster, Tex.). Results of aldosterone and cortisol assays were normalized to cellular protein per well, expressed as pmol per mg cell protein and transformed to percentage of the control response where indicated. $IC_{50}$ values for calmidazolium and KN93 were calculated by taking the difference between basal and stimulated values as 100%.

Protein determination

Cells were solubilized in Tris-HCl (50 mM pH 7.4) containing NaCl (150 mM), SDS (1%), EGTA (5 mM), $MgCl_2$ (0.5 mM), $MnCl_2$ (0.5 mM), and phenylmethylsulfonylfluoride (PMSF 0.2 mM), and stored frozen at −20° C. Protein content of samples was then determined by the bicinchoninic acid protein assay, using the BCA assay kit (Pierce, Rockford, Ill.).

Immunoblot analysis

For each treatment, cells were solubilized as described above and an equivalent amount of protein (30 μg) for each sample were separated by SDS-PAGE (12.5%) and then electrophoretically transferred to polyvinylidene difluoride membrane as previously described (Clark et al (1994) J. Biol. Chem., 269:2831–322, reference specifically incorporated herein by reference). Immunoblot analysis was as described (Id) using a rabbit sera containing the specific StAR antipeptide antibody (see ANTIBODIES infra) as the primary label and a donkey anti-rabbit IgG conjugated with horseradish peroxidase (Amersham, Arlington Heights, Ill.). The specific signal was detected by chemiluminescence assays using the Renaissance kit from DuPont NEN (Boston, Mass.) and the StAR specific bands were quantitated by BioImage Visage 2000 computer-assisted image analysis (BioImage, Ann Arbor, Mich.). Different exposure times were used to insure linearity.

Statistical analysis

Statistical analysis of the data was by analysis of variance, followed by Student-Newman-Keuls multiple comparison analysis or, for transformed data, by the Mann-Whitney U test.

KN93 effects on StAR induction

The data above suggest that CaM kinase II plays a role in steroidogenesis prior to P450scc conversion of cholesterol to pregnenolone. StAR protein levels were elevated by Ang II, $K^+$, and Bay K in H295R cells. To discriminate between the potential sites of CaM kinase II involvement in aldosterone production, the effects of KN93 on StAR protein expression were also examined. Agonist-induction of StAR protein expression was not affected by co-treatment with KN93 at a concentration (3 μM) which potently inhibited aldosterone production.

EXAMPLE 12

Transcription Repressor DAX-1 Inhibits StAR mRNA and Protein Synthesis; Role of StAR in Screening for DSS The overexpression of DAX-1 in Y-1 adrenal tumor cells results in a complete inhibition of steroid synthesis and an accompanying inhibition of StAR mRNA and protein synthesis. The present example demonstrates this phenomenon.

Male to female sex reversal has been observed in individuals with duplications of the short arm of the X chromosome. The study of Xp duplicated patients demonstrated that sex reversal results from the presence of two active copies of the DSS (Dosage Sensitive Sex Reversal) locus. A double dosage of the DSS disrupts testis formation while its absence is compatible with a male phenotype, suggesting a role for DSS in ovarian development and as a link between ovary and testis formation. DSS has been mapped to a 160-bp region of human chromosome Xp21, which includes the adrenal hypoplasia congenita (AHC) locus.

It is contemplated by the present inventors that the DSS is DAX-1, an unusual member of the nuclear hormone receptor superfamily. DAX-1 maps to the DSS critical region, and is responsible for X-linked adrenal hypoplasia congenita (See Swain et al. 1996, Nature Genetics, 12: 404–409).

The present inventors contemplate that when a double dose of DSS is present, it can bind to SF1 sites at a higher amount than usual, thus turning off SF1 gene (such as StAR, p450 and 3-bHSD). One would expect to see no testosterone synthesized, and the male sex organs would not develop. Hence, the present observation that DAX-1 inhibits StAR synthesis suggests a use of StAR nucleic acid in a screening assay for the disease DSS and constitutes a method of use as part of the present invention.

Screening for Dosage Sensitive Sex Reversal

The present example describes the utility of using mouse StAR mRNA sequence, or the StAR mRNA sequence as defined in SEQ ID NO:14, which is the coding region of the mouse mRNA sequence from nucleotide position 210 to 931, in a screening assay for DSS. This region shares about 84% identity with the human StAR mRNA sequence from nucleotide position 267 to 988 (SEQ ID NO: 15), in a method for screening a patient sample for Dosage Sensitive Sex Reversal (DSS). The screening procedure may also be conducted using the nucleic acid sequence, SEQ ID NO: 15, or a fragment of that sequence. It is anticipated that any of the primers described herein may be used as a PCR primer to generate an about 400 bp piece of nucleic acid that may be used for the present screening assay.

A tissue sample from a patient to be screened would be tested to determine the presence of nucleic acid that demonstrated hybridization to the probe sequence for StAR by RT-PCR using any one of the above described StAR encoding sequences. If presence of StAR nucleic acid is detected, the patient sample will be determined not to evidence DSS. If presence of StAR nucleic acid is detected, then the patient will be determined to have DSS, or to be at risk of developing this disease. This screening protocol may be used together with or clinically detectable symptoms of the patient in determining the appropriate treatment for the patient.

Children diagnosed with DSS have been found to have elevated, and most times twice, the level of a mutated form of the protein, DAX-I (See Zanaria et al. (1994) *Nature* 372(15):635–641). DSS is a disease that affects primarily males, and that causes afflicted males to phenotypically revert to females. (See Namabe et al. (1992) *Hum. Genet.,* 90:211–214). The present invention contemplates the use of StAR in the diagnosis of this disease, as it is contemplated that the StAR gene is not functional or is not expressed at sufficient levels in these patients, thus resulting in the phenotypically detectable sex reversal.

EXAMPLE 13

Mouse StAR Transcripts and Human StAR Transcripts Specific for StAR mRNA

Three transcripts specific for StAR mRNA have been detected in the mouse (~1.6 kb, ~2.7 kb, and ~3.4 kb) and in the human (~1.6 kb, ~4.4 kb, and ~7.5 kb).

Differences in the lengths between the mouse and human transcripts were identified. The difference in length is attributed, at least in part, to a difference in the length of the 3'-intranslated regions.

The additional length was determined to exist at a site 31 of the XhoI cleavage site, as determined in the following study:

Digest λ DNA purified from bacteriophage with Not 1/Sal 1/XHo 1 to release the Not 1 and Sal 1 insert (cloning strategy) and Xho 1 to determine which end of the cDNA has the additional sequences.

Results: StAR cDNA

Clone 1 (StAR cDNA)-1500 bp, mouse StAR sequence expect-611 bp and 939 bp fragments Clone 2 (FP#1)-1500 bp Clone 3 (FP#12)-1650 bp Clone 4 (FP#5)-2400 bp Clone 5 (FP#7)-2400 bp Clone 6 (FP#16)-2350 bp Clone 7 (FP#13)-2800 bp Conclusion: additional length in human StAR cDNA is 3' of the Xho 1 site.

EXAMPLE 14

Mouse StAR Identity to Other Species

Full length cDNA clones for StAR have been isolated for the mouse and human (FIG. 3). cDNA for human StAR was isolated from a human adrenal library. The deduced amino acid sequence from the human StAR DNA was about 87% identical to the mouse sequence. The cDNA's have approximately 84% homology. The structural gene for StAR has also been isolated and characterized for both the mouse and human. The genes span 6.5 kb in the mouse and 8 kb in the human with the intronic sequences contributing to increased length in the human. Both are organized into seven exons and six introns with exons III–XI being of identical size.

A StAR pseudogene was identified by RT-PCR amplification of RNA from human testis and PCR amplification of human genomic DNA (Sugawara et al (1995), Lin et al. (1995)). Sequence analysis of the pseudogene indicated that it lacks introns and has several nucleotide insertions, deletions, and substitutions (Sugawara et al. (1995)). However, detection by RT-pCR suggests that the pseudogene is transcribed.

Southern blotting of somatic cell hybrids followed by fluorescent in situ hybridization was used to map the human structural gene to chromosome 8p.11.2 and the pseudogene to chromosome 13 (Sugawara et al (1995)). The human promoter, a 1.3-kb upstream sequence, can confer both basal and cAMP-dependent transcriptional activation of a luciferase reporter gene in Y1 mouse adrenal cells (Id). Similarly, ~1 kb of the 5'-upstream sequence of the mouse StAR gene has been observed to drive expression of human GH reporter in Y1 cells. The suggestion that StAR is a potential target for SF-1 is supported in studies that demonstrate that SF-1 binds to both the murine and human promoters and contributes to the transcriptional activity of StAR.

StAR protein sequence is highly conserved with 85%–88% identity and greater than 90% similarity in the species studied to date (FIG. 5). In addition, a partial cDNA has been isolated from the sheep that has 80% identity with the corresponding regions of the other species. The greatest divergence appears to center around the putative mitochondrial signal sequence cleavage site described here for the mouse sequence. This region of the protein contains an amino acid motif that is highly conserved in presequences that undergo a sequential two-step cleavage by the matrix-processing protease and the mitochondrial intermediate-processing peptide, respectively.

The submitochondrial location of StAR has been determined using protein-A gold labeling of immuno-reacted StAR in mouse adrenal zona fasciculata cells. Colloidal gold particles were concentrated within the mitochondria to the intermembrane space and the intermembrane space side of the cristae membrane (King et al (1995)).

In vitro transcription/translation systems have been used to demonstrate that isolated mitochondria are competent to import and process both mouse and bovine StAR protein. Rat heart mitochondria were used for the import assay with bovine StAR, indicating import of StAR is not dependent upon factors specific to mitochondria isolated from steroidogenic tissues. The ability of StAR to increase steroid production has also been confirmed in an in vitro reconstituted system. StAR protein added to mitochondria isolated from MA-10 mouse Leydig tumor cells has been observed to result in a time- and dose-dependent increase in pregnenolone synthesis. This stimulation was shown to be specific for StAR in that pregnenolone synthesis was not affected by addition of another mitochondrial imported protein, adrenodoxin.

Computer analysis of the StAR protein sequence has identified three putative PKA/Cam kinase II phosphorylation sites and one PKC phosphorylation site (FIG. 5). Site-directed mutagenesis of StAR cDNA, which changes these putative target residues, will be used to determine if the phosphorylation of StAR itself is required for mitochondrial import, and that phosphorylation of StAR is directly linked to the steroidogenic response of the cell to hormone stimulation.

The high degree of similarity between the nucleotide sequence for the mouse and human StAR does not extend into the 5'-flanking regions of the genes. However, the human StAR promoter also contains a putative SF-1/AdBP4 binding site located −926/−918 relative to the start site of transcription in addition to two putative Sp1 consensus consequences (Sugawara et al (1995)).

The coding region of the human StAR cDNA has been characterized and is shown in SEQ ID NO:19. The coding nucleotides are capitalized, whereas the untranslated nucleotides are in lowercase.

Toward more definitive studies on the mechanisms regulating StAR gene expression, approximately 1 kb and 1.3 kb of the 5'-flanking regions of the mouse and human gene, respectively, have been isolated and sequenced. Inspection of the murine StAR promoter does not provide many clues to putative cis-acting regulatory elements; it lacks a canonical TATA box and does not contain a consensus cAMP-responsive element. Thus, like most of the cytochrome P450 steroid hydroxylase genes that are also regulated by cAMP but lack classical CREs, the regulatory regions of StAR may be unique.

EXAMPLE 15

StAR is Regulated by Oestradiol

This present study demonstrates that oestradiol alters components of the steroidogenic pathway between cholesterol and P450 scc.

Oestradiol inhibits testosterone (T) secretion in rams, and at least part of this action is gonadotrophin-independent. There is therefore a local effect on testicular steroidogenesis. Low-titre immunization of rams against oestradiol increases T secretion without affecting testicular steroidogenic enzyme activity or expression. Adult rams, during the breeding and nonbreeding seasons, were injected (iv every 3–4 days) with enough oestradiol antiserum to maintain an antibody titre of about 1:200. At this titre, the antibody does not cross-react with T. Blood samples were taken every 20 minutes for 10 h (d 21 of immunization) for pulsatile T and LH measurements. Pooled samples were used for assay of cholesterol, HDL and LDL+VLDL concentrations. The testes were then removed and RNA extracted for measurement of LDL receptor and StAR mRNA levels.

Mean, basal plasma T concentrations were not altered by treatment or by season ($P \leqq 0.05$). Relative levels of StAR mRNA were 67% higher in breeding vs nonbreeding season ($P<0.01$), and 21% higher in immune vs control rams ($P<0.05$) irrespective of season. Low-titre oestradiol immunization increases T secretion by increasing StAR mRNA abundance and thus the delivery of cholesterol to P450scc. These data provide evidence that StAR is regulated by oestradiol in the testis.

EXAMPLE 16

Binding of StAR Protein to a Mitochondrial Membrane Protein Complex

The following studies demonstrates that cholesterol transfers to the inner mitochondrial membrane only as StAR protein is being imported.

A protein complex was purified from MA-10 cell mitochondrial membranes using an affinity column constructed by crosslinking the C-terminus of commercially synthesized StAR signal peptide to Sepharose 4B beads modified with hydrazine. Specific binding of StAR signal peptide to the complex was examined. When biotinylated StAR signal peptide was incubated with the protein complex, followed by crosslinking with disuccinimidyl suberate, it shifted in size from 3.5 kDa to approximately 300 kDa upon one dimensional SDS polyacrylamide gel electrophoresis. The binding of biotinylated StAR signal peptide to the protein complex was completely inhibited by preincubation with 200 $\mu$M unlabeled StAR signal peptide. Conversely, preincubation with 200 $\mu$M of the signal peptide of ornithine transcarbamylase (OTC) or 100 $\mu$M of the signal peptide of the F1-ATPase-β subunit, two other mitochondrial proteins, did not show similar inhibitory effects on binding. This protein complex was then incorporated into liposomes for further examination. Incubation of $^{35}$S-labled StAR signal peptide with the liposomes resulted in a sharp peak of radioactivity which co-eluted with the liposome fraction recovered from a Sepharcyl S-200 column. Preincubation of unlabeled StAR signal peptide with the liposomes reduced total radioactivity by 65% in this fraction, whereas OTC signal peptide did not reduce the binding to the liposomes. These results suggest that the signal region of the StAR protein is capable of specifically binding to a mitochondrial membrane protein complex.

EXAMPLE 17

Corticotropin-Releasing Hormone (CRH) and Testosterone—Effects of StAR

CRH treatment of MA-10 mouse Leydig tumor cells results in a dose dependent stimulation of testosterone production (Biol Reprod 53:620–626 (1995)). In view of this observation, the effects of CRH on the synthesis of the StAR protein in these cells was examined.

Treatment of MA-10 cells with CRH resulted in a dose-dependent increase in the synthesis of the StAR protein with a maximal response observed at 1 $\mu$M. The maximal response to 1 $\mu$M CRH was seen at 4 hr following stimulation. Treatment with the cAMP analog, dbcAMP, also resulted in a dose-dependent increase in both StAR and steroid synthesis, reaching a maximum at 1 $\mu$M. The maximum response to dbcAMP occurred at 6 hr post stimulation. While hCG treatment of MA-10 cells also resulted in an increase in StAR synthesis, the levels obtained were significantly lower than those seen with CRH or dbcAMP. CRH treatment in the presence of hCG resulted in a higher level of StAR synthesis than that seen with maximal doses of CRH or hCG alone. These results indicate that CRH, like hCG and dbcAMP, can stimulate the synthesis of testosterone in MA-10 Leydig tumor cells and apparently does so by increasing the synthesis of the StAR protein.

EXAMPLE 18

StAR as a Cholesterol Binding Protein

The present study demonstrates the cholesterol binding capacity of StAR and its potential utility for binding and hence use in the regulation and/or reduction of cholesterol.

For these studies StAR proteins were obtained from three sources; (1) MA-10 cells stimulated with dbAMP; (2) monkey kidney cells (COS 1) transfected with StAR cDNA; and (3) expression of a recombinant pKK233-2/StAR plasmid in *E. coli.* Filtration radioassays and Steady-State (native) polyacrylamide gel electrophoresis were used to detect cholesterol binding to StAR. Results from these radioassays demonstrated low levels of specific binding (20–40% of the total binding) of cholesterol to StAR. Fluorescent sterol binding assay results support the finding that the binding of NBD-cholesterol to StAR occurs with an affinity in the nanomolar range. Thus, this study has provided evidence that cholesterol can bind to the StAR protein with high affinity.

EXAMPLE 19

StAR Binding Site for SF-1 AdBP4

In the mouse, a sequence motif that matches the known requirements for binding the orphan nuclear receptor, SF-1/AdBP4, is located at position −128/−135 relative to the transcriptional start site. SF-1/AdBP4 binding sites are present in the promoters of all the steroid hydroxylase genes, and SF-1/AdBP4 has been shown to transcriptionally regulate their expression in a cAMP-dependent manner. Thus, StAR may represent another target for SF-1/AdBP4.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Alberta et al., (1989) *J. Biol. Chem.* 264, 2368–2372.
Almahbobi, et al., (1992) *Exp. Cell Res.* 200, 361–369.
Andersson, et al., (1989) *J. Biol. Chem.* 264, 8222–8229.
Ardail, et al., (1991) *J. Biol. Chem.* 266, 7978–7981.
Ascoli, M. (1981) *Endocrinology* 108, 88–95.
Bonner and Laskey, (1974) *Eur. J. Biochem.* 46, 83–88.
Bradford, M. (1976) *Anal. Biochem.* 72, 248–254.
Brown, et al., (1992) *Mol. Cell. Endrocrinol.* 83, 1–9.
Camacho, et al., *J. Clin. Endocrinol. Metab.* 28:153–161, 1968.
Caracciolo et al. (1989) *Science,* 245:1107.
Chanderbhan, et al., (1982) *J. Biol. Chem.* 257, 8928–8934.
Chomczynski and Sacchi, (1987) *Anal. Biochem.* 162, 156–159.
Clark and Waterman, (1991) *J. Biol. Chem.* 266, 5898–5904.
Cooke, et al., (1975) *Biochem. J.* 150, 413–418.
Crivello and Jefcoate, (1980) *J. Biol. Chem.* 255, 8144–8151.
Davis and Garren, (1968) *J. Biol. Chem.* 243, 5153–5157.
Degenhart, et al., *Acta Endocrinologia* 71:512–518, 1972.
Deutscher, (1990) *Methods in Enzymology,* 182, *Guide to Protein Purification,* Academic Press, Inc.
Elliott, et al., (1993) *Endocrinology* 133, 1669–1677.
Epstein and Orme-Johnson, (1991) *J. Biol. Chem.* 266, 19739–19745.
Ferguson, (1963) *J. Biol. Chem.* 238, 2754–2759.
Freeman, (1987) *J. Biol. Chem.* 262, 13061–13068.
Garnier, et al., (1993) *Endocrinology* 132, 444–458.
Garren, et al., (1965) *Biochemistry* 53, 1443–1450.
Glick, et al., (1991) *Trends Cell Biol.* 1, 99–103.
Green and Orme-Johnson, (1991) *J. Steroid Biochem. Molec. Biol.* 40, 421–429.
Hall and Almahbobi, (1992) *J. Steroid Biochem. Molec. Biol.* 43, 769–777.
Hartl, F-U. (1986) *Cell* 47, 939–951.
Hauffa, et al., *Clin. Endocrinol.* 23:481–493, 1985.
Hawley-Nelson, et al., (1993) *Focus* 15, 73–79.
Haynes, et al., (1959) *J. Biol. Chem.* 234, 1421–1423.
Hendrick, et al., (1989) Proc. Natl. Acad. Sci. U.S.A. 86, 4056–4060.
Jefcoate, et al., (1987) *J. Steroid Biochem.* 27, 721–729.
Jefcoate, et al., (1986) *Endocr. Res.* 12, 315–350.
Jefcoate, et al., (1992) *J. Steroid Biochem. Molec. Biol* 43, 751–767.
Jefcoate, et al., (1974) *Eur. J. Biochem.* 42, 539–551.
Kalousek, et al. (1988) *Proc. Natl. Acad. Sci U.S.A.* 85, 7536–7540.
Karboyas and Koritz, (1965) *Biochemistry* 4, 462–468.
Kiebler, et al., (1993) *J. Memb. Biol.* 135, 191–207.
Koizumi et al., *Clin. Chim. Acta* 77:301–306, 1977.
Krueger and Orme-Johnson, (1983) *J. Biol. Chem.* 258, 10159–10167.
Laemmli, U. K. (1970) *Nature* 227, 680–688.
Lin et al., *J. Clin. Invest.* 88:1955–1962, 1991.
Mendelson, et al., (1975) *Biochem. Biophys. Acta* 411, 222–230.
McEnery, et al., (1992) *Proc. Natl. Acad. Sci. U.S.A.* 89, 3170–3174.
Merrifield, R. *J. Am. Chem. Soc.,* 85:2149, 1963.
Mertz and Pedersen, (1989) *Endocr. Res.* 15, 101–115.
O'Farrell, P. H. (1975) *J. Biol. Chem.* 250, 4007–4021.
Pedersen and Brownie, (1983) *Proc. Natl. Acad. Sci U.S.A.* 80, 1882–1886.
Pedersen and Brownie, (1987) *Science* 236, 188–190.
Pon et al., (1986) *J. Biol. Chem.* 261, 13309–13316.
Pon et al., (1986) *Endocr. Res.* 12, 429–446.
Privalle, et al., (1983) *Proc. Natl. Acad. Sci. U.S.A.* 80, 702–706.
Python, et al., (1993) *Endocrinology* 132, 1489–1496.
Reddy, et al., (1993) *BioTechniques* 15, 444–448.
Remington: The Science and Practice of Pharmacy, 19th edition, Volumes 1 and 2, A. R. Gennaro, ed. Mack Publishing Co. Easton, Pa., 1995.

Resko, et al. (1974) *Endocrinology* 94, 128–135.
Sambrook, et al., (1989) *Molecular Cloning, A Laboratory Manual,* 2nd Ed., Cold Springs Harbor Laboratory, Cold Springs Harbor, N.Y.
Saiki, et al., (1988) *Science* 239, 487–494.
Sala, et al., (1979) *J. Biol. Chem.* 254, 3861–3865.
Sanger, et al., (1977) *Proc. Natl. Acad. Sci. U.S.A.* 74, 5463–5467.
Schleyer and Neupert, (1985) *Cell* 43, 339–350.
Schwaiger, et al., (1987) *J. Cell Biol.* 105, 235–246.
Simbeni, et al., (1990) *J. Biol. Chem.* 265, 281–285.
Simbeni, et al., (1991) *J. Biol. Chem.* 266, 10047–10049.
Simpson, et al., (1972) *Eur. J. Biochem.* 28, 442–450.
Stocco and Kilgore, (1988) *Biochem. J.* 249, 95–103.
Stocco and Chaudhary, (1990) *Cell. Signal.* 2, 161–170.
Stocco and Chen, (1991) *Endocrinology* 128, 1918–1926.
Stocco and Sodeman, (1991) *J. Biol. Chem.* 266, 19731–19738.
Stocco, D. M. (1992) *J. Steroid Biochem. Molec. Biol.* 43, 319–333.
Stocco and Ascoli, (1993) *Endocrinology* 132, 959–967.
Stocco, et al., (1993) *Endocrinology* 133, 2827–2832.
Stocco and Clark, (1993) *J. Steroid Biochem. Mole. Biol.* 46, 337–347.
Stone and Hechter, (1954) *Arch. Biochem. Biophysics* 51, 457–469.
Towbin, et al., (1979) *Proc. Natl. Acad. Sci. U.S.A.* 76, 4350–4354.
van Amerongen, et al., (1989) *Biochem. Biophys. Acta.* 1004, 36–43.
von Heigne, G. (1986) *EMBO J.* 5, 1335–1342.
von Heijne, et al., (1989) *Eur. J. Biochem.* 180, 535–545.
Guo, et al. (1995) *JAMA* 274, 324–330.
Yanase, et al. (1996) *J. Clin. Endocrinol. Metab.* 81, 530–535..
Muscatelli, et al. (1994) *Nature* 372, 672–676.
Zanaria, et al. (1994) *Nature* 372, 635–641.
Swain, et al. (1996) *nature Genetics* 12, 404–409.

What is claimed is:

1. A purified polypeptide consisting of a contiguous amino acid sequence in accordance with SEQ ID NO: 3, SEQ ID NO: 4, SEQ ID NO: 5, SEQ ID NO: 6, SEQ ID NO: 7, or SEQ ID NO: 8.

2. A purified polypeptide consisting of a contiguous amino acid sequence having a 70 to 99% identity to one of the group consisting of SEQ ID NO: 3, SEQ ID NO: 4, SEQ ID NO: 5, SEQ ID NO: 6, SEQ ID NO: 7 and SEQ ID NO: 8.

* * * * *

SEQUENCE LISTING

```
<160> NUMBER OF SEQ ID NOS: 19

<210> SEQ ID NO 1
<211> LENGTH: 1466
<212> TYPE: DNA
<213> ORGANISM: Mus sp.

<400> SEQUENCE: 1

gtcgacccac gcgtccgctc aggaccttga aaggctcagg aagaacaacc cttgagcacc     60

tcagcactca gcatgttcct cgctacgttc aagctgtgtg ctggaagctc ctatagacat    120

atgcggaata tgaaaggatt aaggcaccaa gctgtgctgg ccattggcca agagctcaac    180

tggagagcac tgggggattc cagtcccggg tggatgggtc aagttcgacg tcggagctct    240

ctgcttggtt ctcaactgga agcaacactc tatagtgacc aggagctgtc ctacatccag    300

cagggagagg tggctatgca gaaggccttg ggcatactca acaaccagga aggctggaag    360

aaggaaagcc agcaggagaa cggggacgaa gtgctaagta agatggtgcc agatgtgggc    420

aaggtgtttc gcttggaggt ggtggtagac cagcccatgg acagactcta tgaagaactt    480

gtggaccgca tggaggccat gggagagtgg aacccaaatg tcaaggagat caaggtcctg    540

cagaggattg gaaaagacac ggtcatcact catgagctgg ctgcggcggc agcaggcaac    600

ctggtggggc ctcgagactt cgtgagcgtg cgctgtacca agcgcagagg ttccacctgt    660

gtgctggcag gcatggccac acattttggg gagatgccgg agcagagtgg tgtcatcaga    720

gctgaacacg gccccacctg catggtgctt catccactgg ctggaagtcc ctccaagact    780

aaactcactt ggctgctcag tattgacctg aaggggtggc tgccgaagac aatcatcaac    840

caggtcctat cgcagaccca gatagagttc gccaaccacc tgcgcaagcg cctggaagcc    900

agccctgcct ctgaggccca gtgttaagga ctgtccacca cattgacctg caaatcattg    960

gaagctctca caggaagcct gcaagtctgt ccatcttcag ctaacagcat cgggaggggt   1020

ggtagtcagg agacactagg actgactggt aaaatcagga tcagcaaaat agaaatgagg   1080

cttagaataa aagttctcta gtgtctccca ctgcatagct gtgaaggcta agggataagt   1140

agctatgaaa cctttcatct aggcttgtat atgctgacct aaaagacacc agcagctacg   1200

aacaggggat gctaaggatc gggaactgtt gtcttaccag ctccaaatgt cactacctga   1260
```

-continued

```
aggcagtgtg cacacaaagc aaggtcttgc ctaggaaact ctgtaaaagt tctcctctgt   1320

aaaaggccag aacttgaatg aaactaccta caaagggcct ttccagagta ttccaacttt   1380

tctctgagga gaaatgaaac catcattgtg ccgacttccc tactaatccc atgacaataa   1440

agaacataca taaaaaaaaa aaaaaa                                        1466
```

```
<210> SEQ ID NO 2
<211> LENGTH: 284
<212> TYPE: PRT
<213> ORGANISM: Mus sp.

<400> SEQUENCE: 2

Met Phe Leu Ala Thr Phe Lys Leu Cys Ala Gly Ser Ser Tyr Arg His
1               5                   10                  15

Met Arg Asn Met Lys Gly Leu Arg His Gln Ala Val Leu Ala Ile Gly
            20                  25                  30

Gln Glu Leu Asn Trp Arg Ala Leu Gly Asp Ser Ser Pro Gly Trp Met
        35                  40                  45

Gly Gln Val Arg Arg Arg Ser Ser Leu Leu Gly Ser Gln Leu Glu Ala
    50                  55                  60

Thr Leu Tyr Ser Asp Gln Glu Leu Ser Tyr Ile Gln Gln Gly Glu Val
65                  70                  75                  80

Ala Met Gln Lys Ala Leu Gly Ile Leu Asn Asn Gln Glu Gly Trp Lys
                85                  90                  95

Lys Glu Ser Gln Gln Glu Asn Gly Asp Glu Val Leu Ser Lys Met Val
            100                 105                 110

Pro Asp Val Gly Lys Val Phe Arg Leu Glu Val Val Val Asp Gln Pro
        115                 120                 125

Met Asp Arg Leu Tyr Glu Glu Leu Val Asp Arg Met Glu Ala Met Gly
    130                 135                 140

Glu Trp Asn Pro Asn Val Lys Glu Ile Lys Val Leu Gln Arg Ile Gly
145                 150                 155                 160

Lys Asp Thr Val Ile Thr His Glu Leu Ala Ala Ala Ala Ala Gly Asn
                165                 170                 175

Leu Val Gly Pro Arg Asp Phe Val Ser Val Arg Cys Thr Lys Arg Arg
            180                 185                 190

Gly Ser Thr Cys Val Leu Ala Gly Met Ala Thr His Phe Gly Glu Met
        195                 200                 205

Pro Glu Gln Ser Gly Val Ile Arg Ala Glu His Gly Pro Thr Cys Met
    210                 215                 220

Val Leu His Pro Leu Ala Gly Ser Pro Ser Lys Thr Lys Leu Thr Trp
225                 230                 235                 240

Leu Leu Ser Ile Asp Leu Lys Gly Trp Leu Pro Lys Thr Ile Ile Asn
                245                 250                 255

Gln Val Leu Ser Gln Thr Gln Ile Glu Phe Ala Asn His Leu Arg Lys
            260                 265                 270

Arg Leu Glu Ala Ser Pro Ala Ser Glu Ala Gln Cys
        275                 280
```

```
<210> SEQ ID NO 3
<211> LENGTH: 14
<212> TYPE: PRT
<213> ORGANISM: Mus sp.

<400> SEQUENCE: 3
```

-continued

```
Ala Glu His Gly Pro Thr Cys Met Val Leu His Pro Leu Ala
1               5                   10


<210> SEQ ID NO 4
<211> LENGTH: 12
<212> TYPE: PRT
<213> ORGANISM: Mus sp.

<400> SEQUENCE: 4

Ala Leu Gly Ile Leu Asn Asn Gln Glu Gly Trp Lys
1               5                   10


<210> SEQ ID NO 5
<211> LENGTH: 19
<212> TYPE: PRT
<213> ORGANISM: Mus sp.

<400> SEQUENCE: 5

Gly Ser Thr Cys Val Leu Ala Gly Met Ala Thr His Phe Gly Glu Met
1               5                   10                  15

Pro Glu Gln


<210> SEQ ID NO 6
<211> LENGTH: 6
<212> TYPE: PRT
<213> ORGANISM: Artificial
<220> FEATURE:
<223> OTHER INFORMATION: Synthesized peptide of the StAR protein

<400> SEQUENCE: 6

Asn Gln Glu Gly Trp Lys
1               5


<210> SEQ ID NO 7
<211> LENGTH: 9
<212> TYPE: PRT
<213> ORGANISM: Artificial
<220> FEATURE:
<223> OTHER INFORMATION: Synthesized peptide of the StAR protein

<400> SEQUENCE: 7

Ala Glu His Gly Pro Thr Cys Met Val
1               5


<210> SEQ ID NO 8
<211> LENGTH: 11
<212> TYPE: PRT
<213> ORGANISM: Mus sp.

<400> SEQUENCE: 8

Ile Leu Asn Asn Gln Glu Gly Trp Lys Lys Glu
1               5                   10


<210> SEQ ID NO 9
<211> LENGTH: 25
<212> TYPE: DNA
<213> ORGANISM: Mus sp.
<220> FEATURE:
<221> NAME/KEY: misc_feature
<222> LOCATION: (3)..(3)
<223> OTHER INFORMATION: n = (a or c or g or t/u) or (unknown or other)
<220> FEATURE:
<221> NAME/KEY: modified_base
<222> LOCATION: (6)..(6)
<223> OTHER INFORMATION: r = a or g
<220> FEATURE:
<221> NAME/KEY: modified_base
```

<222> LOCATION: (9)..(9)
<223> OTHER INFORMATION: y = c or t/u
<220> FEATURE:
<221> NAME/KEY: misc_feature
<222> LOCATION: (12)..(12)
<223> OTHER INFORMATION: n = (a or c or g or t/u) or (unknown or other)
<220> FEATURE:
<221> NAME/KEY: misc_feature
<222> LOCATION: (15)..(15)
<223> OTHER INFORMATION: n = (a or c or g or t/u) or (unknown or other)
<220> FEATURE:
<221> NAME/KEY: misc_feature
<222> LOCATION: (18)..(18)
<223> OTHER INFORMATION: n = (a or c or g or t/u) or (unknown or other)
<220> FEATURE:
<221> NAME/KEY: modified_base
<222> LOCATION: (21)..(21)
<223> OTHER INFORMATION: y = c or t/u

<400> SEQUENCE: 9
gcngarcayg gnccnacntg yatgg 25

<210> SEQ ID NO 10
<211> LENGTH: 25
<212> TYPE: DNA
<213> ORGANISM: Mus sp.
<220> FEATURE:
<221> NAME/KEY: modified_base
<222> LOCATION: (5)..(5)
<223> OTHER INFORMATION: r = a or g
<220> FEATURE:
<221> NAME/KEY: misc_feature
<222> LOCATION: (8)..(8)
<223> OTHER INFORMATION: n = (a or c or g or t/u) or (unknown or other)
<220> FEATURE:
<221> NAME/KEY: misc_feature
<222> LOCATION: (11)..(11)
<223> OTHER INFORMATION: n = (a or c or g or t/u) or (unknown or other)
<220> FEATURE:
<221> NAME/KEY: misc_feature
<222> LOCATION: (14)..(14)
<223> OTHER INFORMATION: n = (a or c or g or t/u) or (unknown or other)
<220> FEATURE:
<221> NAME/KEY: modified_base
<222> LOCATION: (17)..(17)
<223> OTHER INFORMATION: r = a or g
<220> FEATURE:
<221> NAME/KEY: modified_base
<222> LOCATION: (20)..(20)
<223> OTHER INFORMATION: y = c or t/u
<220> FEATURE:
<221> NAME/KEY: misc_feature
<222> LOCATION: (23)..(23)
<223> OTHER INFORMATION: n = (a or c or g or t/u) or (unknown or other)

<400> SEQUENCE: 10
ccatrcangt nggnccrtgy tcngc 25

<210> SEQ ID NO 11
<211> LENGTH: 17
<212> TYPE: DNA
<213> ORGANISM: Mus sp.
<220> FEATURE:
<221> NAME/KEY: modified_base
<222> LOCATION: (3)..(3)
<223> OTHER INFORMATION: y = c or t/u
<220> FEATURE:
<221> NAME/KEY: modified_base
<222> LOCATION: (6)..(6)
<223> OTHER INFORMATION: r = a or g
<220> FEATURE:
<221> NAME/KEY: modified_base
<222> LOCATION: (9)..(9)
<223> OTHER INFORMATION: r = a or g
<220> FEATURE:

<221> NAME/KEY: misc_feature
<222> LOCATION: (12)..(12)
<223> OTHER INFORMATION: n = (a or c or g or t/u) or (unknown or other)

<400> SEQUENCE: 11
aaycarcarg gntggaa 17

<210> SEQ ID NO 12
<211> LENGTH: 17
<212> TYPE: DNA
<213> ORGANISM: Mus sp.
<220> FEATURE:
<221> NAME/KEY: misc_feature
<222> LOCATION: (6)..(6)
<223> OTHER INFORMATION: n = (a or c or g or t/u) or (unknown or other)
<220> FEATURE:
<221> NAME/KEY: modified_base
<222> LOCATION: (9)..(9)
<223> OTHER INFORMATION: y = c or t/u
<220> FEATURE:
<221> NAME/KEY: modified_base
<222> LOCATION: (12)..(12)
<223> OTHER INFORMATION: y = c or t/u
<220> FEATURE:
<221> NAME/KEY: modified_base
<222> LOCATION: (15)..(15)
<223> OTHER INFORMATION: r = a or g

<400> SEQUENCE: 12
ttccanccyt cytgrtt 17

<210> SEQ ID NO 13
<211> LENGTH: 401
<212> TYPE: DNA
<213> ORGANISM: Mus sp.

<400> SEQUENCE: 13
aaccaggaag gctggaagaa ggaaagccag caggagaacg gggacgaagt gctaagtaag 60
atggtgccag atgtgggcaa ggtgtttcgc ttggaggtgg tggtagacca gcccatggac 120
agactctatg aagaacttgt ggaccgcatg gaggccatgg gagagtggaa cccaaatgtc 180
aaggagatca aggtcctgca gaggattgga aaagacacgg tcatcactca tgagctggct 240
gcggcggcag caggcaacct ggtggggcct cgagacttcg tgagcgtgcg ctgtaccaag 300
cgcagaggtt ccacctgtgt gctggcaggc atggccacac attttgggga gatgccggag 360
cagagtggtg tcatcagagc tgaacacggc cccacctgca t 401

<210> SEQ ID NO 14
<211> LENGTH: 1466
<212> TYPE: RNA
<213> ORGANISM: Mus sp.

<400> SEQUENCE: 14
gucgacccac gcguccgcuc aggaccuuga aaggcucagg aagaacaacc cuugagcacc 60
ucagcacuca gcauguuccu cgcuacguuc aagcugugug cuggaagcuc cuauagacau 120
augcggaaua ugaaaggauu aaggcaccaa gcugugcugg ccauuggcca agagcucaac 180
uggagagcac ugggggauuc cagucccggg uggaugggucaaguucgacg ucggagcucu 240 cugcuugguu cucaacugga agcaacacuc uauagugacc aggagcuguc cuacauccag 300
cagggagagg uggcuaugca gaaggccuug ggcauacuca acaaccagga aggcuggaag 360
aaggaaagcc agcaggagaa cggggacgaa gugcuaagua agauggugcc agaugugggc 420
aagguguuuc gcuuggaggu ggugguagac cagcccaugg acagacucua ugaagaacuu 480

-continued

```
guggaccgca uggaggccau gggagagugg aacccaaaug ucaaggagau caagguccug     540
cagaggauug gaaaagacac ggucaucacu caugagcugg cugcggcggc agcaggcaac     600
cugguggggc cucgagacuu cgugagcgug cgcuguacca agcgcagagg uuccaccugu     660
gugcuggcag gcauggccac acauuuuggg gagaugccgg agcagagugg ugucaucaga     720
gcugaacacg gccccaccug cauggugcuu cauccacugg cuggaagucc cuccaagacu     780
aaacucacuu ggcugcucag uauugaccug aaggggugge ugccgaagac aaucaucaac     840
cagguccuau cgcagaccca gauagaguuc gccaaccacc ugcgcaagcg ccuggaagcc     900
agcccugccu cugaggccca guguuaagga cuguccacca cauugaccug caaaucauug     960
gaagcucuca caggaagccu gcaagucugu ccaucuucag cuaacagcau cgggaggggu    1020
gguagucagg agacacuagg acugacuggu aaaaucagga ucagcaaaau agaaaugagg    1080
cuuagaauaa aaguucucua gugucuccca cugcauagcu gugaaggcua agggauaagu    1140
agcuaugaaa ccuuucaucu aggcuuguau augcugaccu aaaagacacc agcagcuacg    1200
aacaggggau gcuaaggauc gggaacuguu gucuuaccag cuccaaaugu aacuaccuga    1260
aggcagugug cacacaaagc aaggucuugc cuaggaaacu cuguaaaagu ucuccucugu    1320
aaaaggccag aacuugaaug aaacuaccua caaagggccu uuccagagua uuccaacuuu    1380
ucucugagga gaaaugaaac caucauugug ccgacuuccc uacuaauccc augacaauaa    1440
agaacauaca uaaaaaaaaa aaaaaa                                         1466
```

<210> SEQ ID NO 15
<211> LENGTH: 722
<212> TYPE: DNA
<213> ORGANISM: Homo sapiens

<400> SEQUENCE: 15

```
gtggattaac caggttcggc ggcggagctc tctactcggt tctcggctgg aagagactct      60
ctacagtgac caggagctgg cctatctcca gcagggggag gaggccatgc agaaggcctt     120
gggcatcctt agcaaccaag agggctggaa gaaggagagt cagcaggaca atggggacaa     180
agtgatgagt aaagtggtcc cagatgtggg caaggtgttc cggctggagg tcgtggtgga     240
ccagcccatg gagaggctct atgaagagct cgtggagcgc atggaagcaa tgggggagtg     300
gaaccccaat gtcaaggaga tcaaggtcct gcagaagatc ggaaaagata cattcattac     360
tcacgagctg gctgccgagg cagcaggaaa cctggtgggg ccccgtgact ttgtgagcgt     420
gcgctgtgcc aagcgccgag gctccacctg tgtgctggct ggcatggaca cagacttcgg     480
gaacatgcct gagcagaagg gtgtcatcag ggcggagcac ggtcccactt gcatggtgct     540
tcacccgttg gctggaagtc cctctaagac caaacttacg tggctactca gcatcgacct     600
caaggggtgg ctgcccaaga gcatcatcaa ccaggtcctg tcccagaccc aggtggattt     660
tgccaaccac ctgcgcaagc gcctggagtc ccaccctgcc tctgaagcca ggtgttgaag     720
ac                                                                   722
```

<210> SEQ ID NO 16
<211> LENGTH: 134
<212> TYPE: DNA
<213> ORGANISM: Homo sapiens

<400> SEQUENCE: 16

```
atgctgctag cgacattcaa gctgtgcgct gggagctcct acagacacat gcgcaacatg      60
```

-continued aaggggctga ggcaacaggc tgtgatggcc atcagccagg agctgaaccg gagggccctg 120
gggggcccca cccc 134

<210> SEQ ID NO 17
<211> LENGTH: 19
<212> TYPE: DNA
<213> ORGANISM: Homo sapiens

<400> SEQUENCE: 17
actggaagcc tgcaagtct 19

<210> SEQ ID NO 18
<211> LENGTH: 285
<212> TYPE: PRT
<213> ORGANISM: Homo sapiens

<400> SEQUENCE: 18

```
Met Leu Leu Ala Thr Phe Lys Leu Cys Ala Gly Ser Ser Tyr Arg His
1               5                   10                  15

Met Arg Asn Met Lys Gly Leu Arg Gln Gln Ala Val Met Ala Ile Ser
            20                  25                  30

Gln Glu Leu Asn Arg Arg Ala Leu Gly Gly Pro Thr Pro Ser Thr Trp
        35                  40                  45

Ile Asn Gln Val Arg Arg Arg Ser Ser Leu Leu Gly Ser Arg Leu Glu
    50                  55                  60

Glu Thr Leu Tyr Ser Asp Gln Glu Leu Ala Tyr Leu Gln Gln Gly Glu
65                  70                  75                  80

Glu Ala Met Gln Lys Ala Leu Gly Ile Leu Ser Asn Gln Glu Gly Trp
                85                  90                  95

Lys Lys Glu Ser Gln Gln Asp Asn Gly Asp Lys Val Met Ser Lys Val
            100                 105                 110

Val Pro Asp Val Gly Lys Val Phe Arg Leu Glu Val Val Val Asp Gln
        115                 120                 125

Pro Met Glu Arg Leu Tyr Glu Glu Leu Val Glu Arg Met Glu Ala Met
    130                 135                 140

Gly Glu Trp Asn Pro Asn Val Lys Glu Ile Lys Val Leu Gln Lys Ile
145                 150                 155                 160

Gly Lys Asp Thr Phe Ile Thr His Glu Leu Ala Ala Glu Ala Ala Gly
                165                 170                 175

Asn Leu Val Gly Pro Arg Asp Phe Val Ser Val Arg Cys Ala Lys Arg
            180                 185                 190

Arg Gly Ser Thr Cys Val Leu Ala Gly Met Ala Thr Asp Phe Gly Asn
        195                 200                 205

Met Pro Glu Gln Lys Gly Val Ile Arg Ala Glu His Gly Pro Thr Cys
    210                 215                 220

Met Val Leu His Pro Leu Ala Gly Ser Pro Ser Lys Thr Lys Leu Thr
225                 230                 235                 240

Trp Leu Leu Ser Ile Asp Leu Lys Gly Trp Leu Pro Lys Ser Ile Ile
                245                 250                 255

Asn Gln Val Leu Ser Gln Thr Gln Val Asp Phe Ala Asn His Leu Arg
            260                 265                 270

Lys Arg Leu Glu Ser His Pro Ala Ser Glu Ala Arg Cys
        275                 280                 285
```

<210> SEQ ID NO 19
<211> LENGTH: 1641

-continued

```
<212> TYPE: DNA
<213> ORGANISM: Homo sapiens

<400> SEQUENCE: 19

agaacaccag gtccaggctg cagctgcggg actcagaggc gaacgttgag gggctcagga     60

aggacgaaga accacccttg agagaagagg cagcagcagc gcggcagcag cagcggcagc    120

gaccccacca ctgccacatt tgccaggaaa caatgctgct agcgacattc aagctgtgcg    180

ctgggagctc ctacagacac atgcgcaaca tgaaggggct gaggcaacag gctgtgatgg    240

ccatcagcca ggagctgaac cggagggccc tgggggggcc cacccctagc acgtggatta    300

accaggttcg gcggcggagc tctctactcg gttctcggct ggaagagact ctctacagtg    360

accaggagct ggcctatctc cagcaggggg aggaggccat gcagaaggcc ttgggcatcc    420

ttagcaacca agagggctgg aagaaggaga gtcagcagga caatggggac aaagtgatga    480

gtaaagtggt cccagatgtg ggcaaggtgt tccggctgga ggtcgtggtg gaccagccca    540

tggagaggct ctatgaagag ctcgtggagc gcatggaagc aatgggggag tggaacccca    600

atgtcaagga gatcaaggtc ctgcagaaga tcggaaaaga tacattcatt actcacgagc    660

tggctgccga ggcagcagga aacctggtgg ggccccgtga ctttgtgagc gtgcgctgtg    720

ccaagcgccg aggctccacc tgtgtgctgg ctggcatggc cacagacttc gggaacatgc    780

ctgagcagaa gggtgtcatc agggcggagc acggtcccac ttgcatggtg cttcacccgt    840

tggctggaag tccctctaag accaaactta cgtggctact cagcatccac ctcaaggggt    900

ggctgcccaa gagcatcatc aaccaggtcc tgtcccagac ccaggtggat tttgccaacc    960

acctgcgcaa gcgcctggag tcccaccctg cctctgaagc caggtgttga agaccagcct   1020

gctgttccca actgtgccca gctgcactgg tacacacgct catcaggaga atccctactg   1080

gaagcctgca agtctaagat ctccatctgg tgacagtggg atgggtgggg ttcgtgttta   1140

gagtatgaca ctaggattca gattggtgaa agtttttagt accaagaaaa cagggatgag   1200

ctcttggatt aaaaggtaac ttcattcact gattagctat gacatgaggg ttcaggcccg   1260

ctaaaaataa ttgtaaaact ttttttctgg gcccttatgt acccacctaa aaccatcttt   1320

aaaatgctag tggctgatat gggtgtgggg gatgctaacc acagggcctg agaagtcttg   1380

ctttatgggc tcaagaatgc catgcgctgg cagtacatgt gcacaaagca gaatctcaga   1440

gggtctcctg cagccctctg ctcctcccgg ccgctgcaca gcaacaccac agaacaagca   1500

gcaccccaca gtgggtgcct tccagaaata tagtccaagc tttctctgtg gaaaaagaca   1560

aaactcatta gtagacatgt ttccctattg ctttcatagg caccagtcag aataaagaat   1620

cataattcac acaaaaaaaa a                                              1641
```